(12) United States Patent
Feng et al.

(10) Patent No.: US 8,759,531 B2
(45) Date of Patent: Jun. 24, 2014

(54) PREPARATION METHOD OF FLUORO-SUBSTITUTED DEUTERATED DIPHENYLUREA

(75) Inventors: Weidong Feng, Jiangsu (CN); Xiaoyong Gao, Jiangsu (CN); Xiaojun Dai, Jiangsu (CN)

(73) Assignee: Suzhou Zelgen Biopharmaccceutical Co., Ltd., Jiangsu, P.R. (CN)

( * ) Notice: Subject to any disclaimer, the term of this patent is extended or adjusted under 35 U.S.C. 154(b) by 0 days.

(21) Appl. No.: 13/635,808

(22) PCT Filed: Mar. 17, 2011

(86) PCT No.: PCT/CN2011/071927
§ 371 (c)(1),
(2), (4) Date: Sep. 18, 2012

(87) PCT Pub. No.: WO2011/113368
PCT Pub. Date: Sep. 22, 2011

(65) Prior Publication Data
US 2013/0060043 A1    Mar. 7, 2013

(30) Foreign Application Priority Data

Mar. 18, 2010 (CN) .......................... 2010 1 0127706

(51) Int. Cl.
*C07C 273/18* (2006.01)
*C07C 275/34* (2006.01)
*C07D 213/81* (2006.01)

(52) U.S. Cl.
USPC .............................. 546/298; 546/323; 564/52

(58) Field of Classification Search
None
See application file for complete search history.

(56) References Cited

FOREIGN PATENT DOCUMENTS

| CN | 101676266 A | 3/2010 |
|---|---|---|
| WO | 0042012 A1 | 7/2000 |
| WO | 2005009961 A2 | 2/2005 |
| WO | 2008115263 A2 | 9/2008 |
| WO | 2010135579 A1 | 11/2010 |
| WO | 2010144499 A2 | 12/2010 |

OTHER PUBLICATIONS

Scott Wilhelm and Du-Shieng Chien, Bay 43-9006: Preclinical Data, Current Pharmaceutical Design, Aug. 2002, 2255-2257, Bayer Research Center, Institute for Preclinical Drug Development, Bayer Corporation, Pharmaceutical Division, 400 Morgan Lane, West Haven, CT 06516, USA.
S. Hedbom, S. Steinbild, A. Frost, M. Büchert, C. Unger, O. Christensen, M. Kornacker, D. Voliotis, R. Heinig and K. Mross, Abstract Presentation from the 2007 ASCO Annual Meeting, Journal of Clinical Oncology, Jun. 2007, vol. 25, No. 18S, American Society of Clinical Oncology.
A Phase II Uncontrolled Study of BAY73-4506 in Previously Untreated Patients With Metastatic or Unresectable RCC, http://clinicaltrials.gov/ct2/show/NCT00664326?term= Regorafenib&rank=17 (last visited Sep. 10, 2012).
A. Frost, M. Buechert, C. Unger, O. Christensen, A. Wagner, R. A. Heinig, M. E. Scheulen, D. Strumberg, U. Fasol and K. Mross, Abstract Presentation from the 2008 ASCO Annual Meeting, American Society of Clinical Oncology.
Safety Study of BAY73-4506 in Patients With Hepatocellular Carcinoma, http://clinicaltrials.gov/ct2/show/NCT01003015?term=Regorafenib&rank=19 (last visited Sep. 10, 2012).
Patients With Metastatic Colorectal Cancer Treated With Regorafenib or Placebo After Failure of Standard Therapy, http://clinicaltrials.gov/ct2/show/NCT01103323?term= Regorafenib&rank=21 (last visited Sep. 10, 2012).
Iris Breitkreutz, Marc S Raab, Olaf Christensen, Alexander Zimmerhackl, Jing Zhang, Simona Blotta, Teru Hideshima, Dharminder Chauhan, Scott Wilhelm, Kenneth C Anderson, MD and Klaus Podar, MD, MSC, PhD, The Novel, Orally Available Multi-Kinase Inhibitor BAY 73-4506 in Multiple Myeloma, Blood (ASH Annual Meeting Abstracts), 2008, 112, Abstract 2766, American Society of Hematology.
International Search Report, International Application No. PCT/CN2011/071927, May 26, 2011.

*Primary Examiner* — Janet L Andres
*Assistant Examiner* — Timothy R Rozof
(74) *Attorney, Agent, or Firm* — Roylance, Abrams, Berdo & Goodman, L.L.P.

(57) ABSTRACT

A fluoro-substituted deuterated diphenylurea compound, especially 4-(4-(3-(4-chloro-3-(trifluoromethyl)phenyl)ureido)-3-fluorophenoxy)-2-(N-(methyl-d3))picolinamide, preparing method and use for treating or preventing tumor and relative diseases thereof.

5 Claims, 1 Drawing Sheet

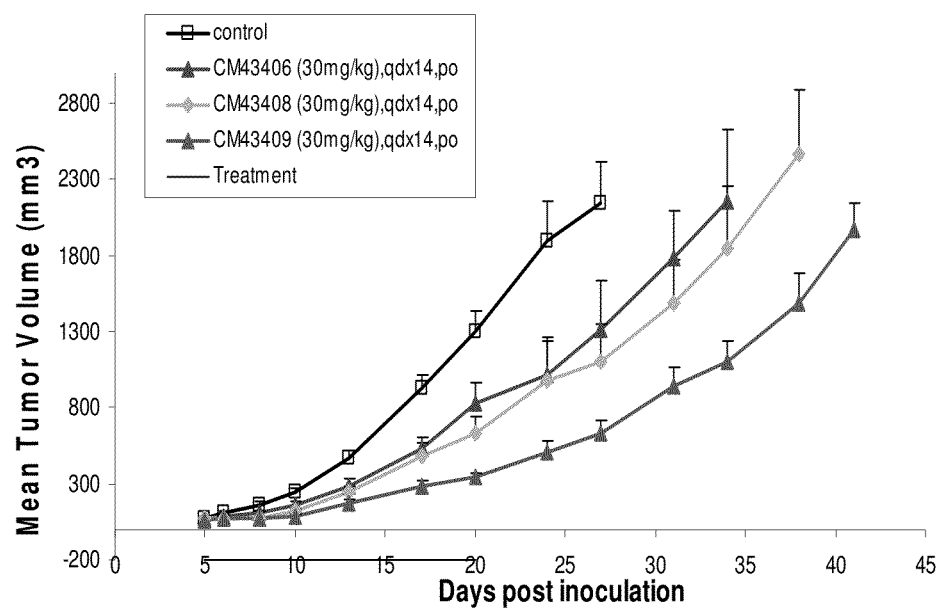

PREPARATION METHOD OF FLUORO-SUBSTITUTED DEUTERATED DIPHENYLUREA

FIELD OF INVENTION

This invention relates to the field of chemical synthesis, and particularly relates to methods and procedures for preparing fluoro-substituted deuterated diphenylurea.

BACKGROUND OF INVENTION

The ω-diphenylurea derivatives are known compounds with c-RAF kinase inhibition activity. For example, WO2000/042012 disclosed a class of ω-carboxyl-aryl-substituted diphenylurea and the use thereof for treating cancer and related diseases.

Initially, ω-diphenylurea compounds, such as Sorafenib, were firstly found as the inhibitor of c-RAF kinase. The other studies had shown that they could also inhibit the MEK and ERK signal transduction pathways and activities of tyrosine kinases including vascular endothelial growth factor receptor-2 (VEGFR-2), vascular endothelial growth factor receptor-3 (VEGFR-3), and platelet-derived growth factor receptor-β (PDGFR-β) (Curr Pharm Des 2002, 8, 2255-2257). Therefore, they were called multi-kinase inhibitors that resulted in dual anti-tumor effects.

Sorafenib (trade name Nexavar), a novel oral multi-kinase inhibitor, was developed by Bayer and Onyx. In December 2005, based on its outstanding performance in phase III clinical trials for treating advanced renal cell carcinoma, Sorafenib was approved by FDA for treating advanced renal cell carcinoma. It was marketed in China in November 2006. However, Sorafenib has various side-effects, such as hypertension, weight loss, rash and so on.

BAY 73-4506 is a 3-fluoro derivative of Sorafenib, and is also a multi-kinase inhibitor targeting tumors and the vessel thereof. In particular, BAY 73-4506 is an effective inhibitor of Raf kinases, p38 kinase, platelet-derived growth factor receptor (PDGFR) kinase and vascular endothelial growth factor receptor (VEGFR) kinase 2 and 3. Inhibition of these special kinases is closely related to the prevention or treatment of osteoporosis, inflammatory diseases, hyperplastic diseases, angiogenic diseases and cancer (Dumas et al., PCT publication WO 2005009961 A2; Hedbom S et al., Journal of Clinical Oncology, 25, (Suppl. 18): Abs, 3593). At present, this compound is in the phase of clinical evaluation for treating renal cell carcinoma (ClinicalTrials.gov Web Site 2008, May 5), solid tumor (J Clin Oncol, 2008, 26(15, Suppl.): Abst 2558), liver cancer (ClinicalTrials.gov Web Site 2010, May 17) and metastatic colon cancer (ClinicalTrials.gov Web Site 2010, May 17). BAY 73-4506 is in the phase of preclinical evaluation for treating multiple myeloma (Blood, 2008, 112 (11): Abst 2766).

However, development of compounds with inhibition efficacy to Raf kinases or better pharmacodynamic properties, and the preparation processes thereof are still in need.

SUMMARY OF INVENTION

The object of the invention is to provide compounds which inhibit raf kinases and has better pharmacodynamic properties and the uses thereof.

Another object of the invention is to provide a series of synthetic methods for deuterated ω-diphenylurea and the intermediates thereof, thereby meeting the production guidances in the pharmaceutical industry and improving the operability and safety.

In the first aspect, the invention provides an intermediate of formula V,

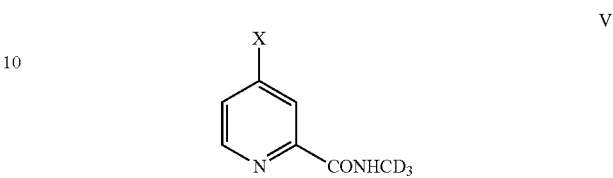

wherein, X is Cl, Br, I, or $OSO_2CF_3$.

In one embodiment, Y is Cl, and the formula is

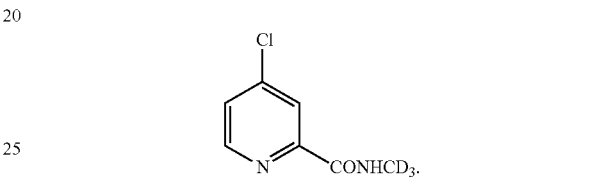

In the second aspect, the invention provides a method for preparing the compound with the following formula,

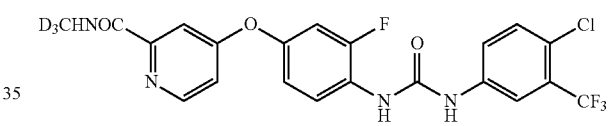

including:
(a) in an inert solvent and in the presence of a base, reacting compound B2 with compound V to form said compound,

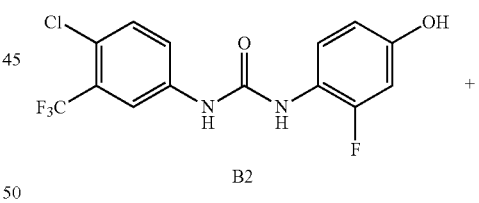

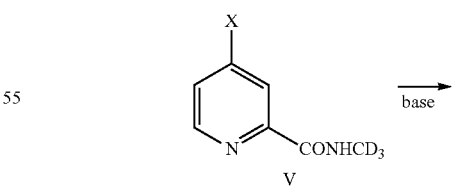

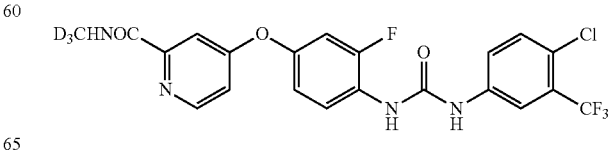

wherein, X is Cl, Br, I, or $OSO_2CF_3$;

or, including:

(b) in an inert solvent, reacting compound B' with CD$_3$NH$_2$ or CD$_3$NH$_2$·HCl to form said compound;

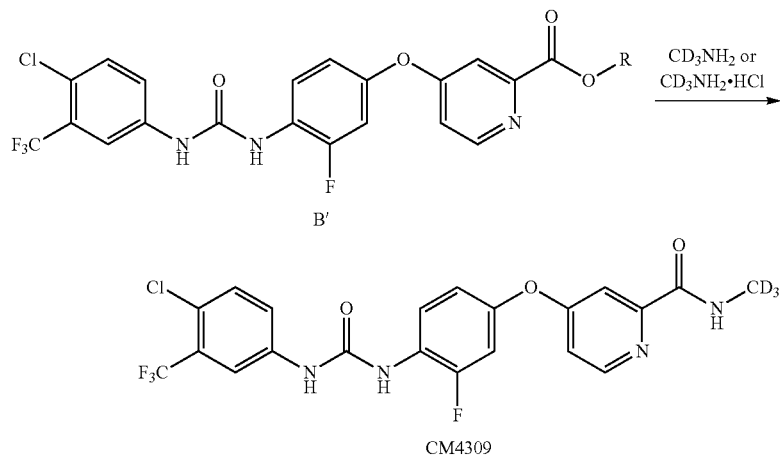

wherein, R is H, straight-chain or branched chain C1-C8 alkyl, or aryl;

or, including:

(c) in an inert solvent, reacting 1-chloro-4-isocyanato-2-(trifluoromethyl)benzene (VIII) with compound 5 to form said compound;

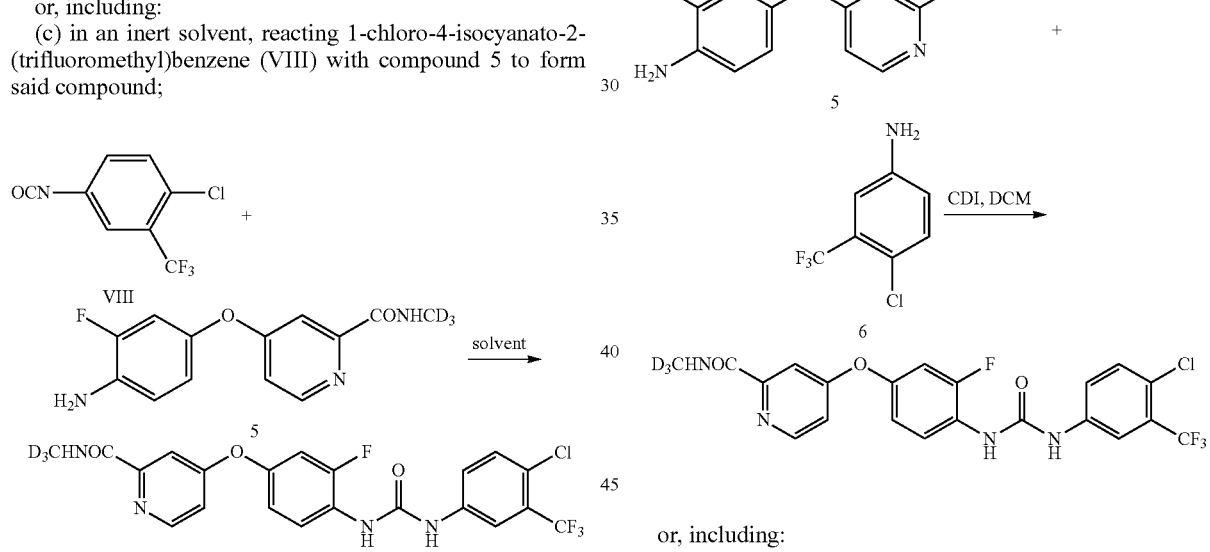

or, including:

(d) in an inert solvent and in the presence of CDI and CH$_2$Cl$_2$, reacting compound 5 with compound 6 to form said compound;

or, including:

(e) in an inert solvent, reacting 3-fluoro-4-aminophenol with compound V to form compound B1; in an inert solvent, reacting compound B1 with compound W to form compound M; and in an inert solvent, reacting compound M with 4-chloro-3-trifluoromethylaniline to form said compound;

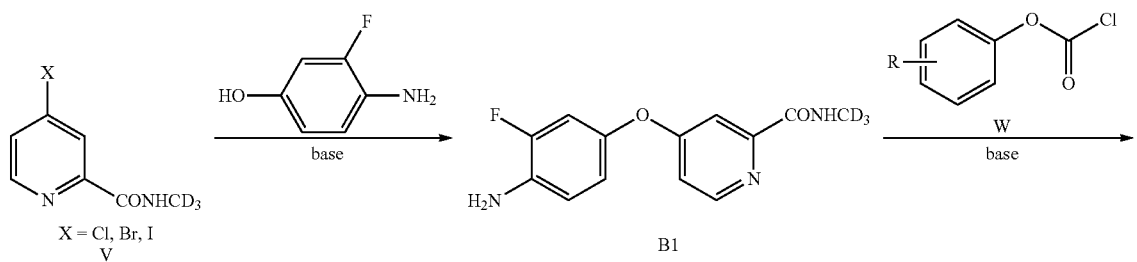

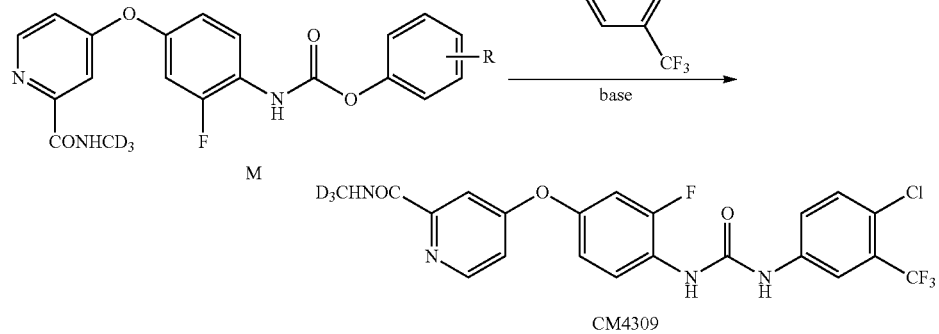

wherein, R is hydrogen, methyl, nitro and chlorine; said inert solvent is selected from chloroform, dichloromethane, tetrahydrofuran, 1,4-dioxane, toluene, pyridine, DMF, DMSO, or the combination thereof; said base is selected from pyridine, potassium carbonate, sodium carbonate, sodium bicarbonate, potassium bicarbonate, triethylamine, N,N-diethyl isopropyl amine, N,N-dimethylamine pyridine, N-methylmorphine, or the combination thereof;

or, including:

(f) in an inert solvent, reacting 4-chloro-3-trifluoromethylaniline with compound W to form compound B; and in an inert solvent, reacting compound B1 with compound B to form said compound;

wherein, R is hydrogen, methyl, nitro and chlorine; said inert solvent is selected from chloroform, dichloromethane, tetrahydrofuran, 1,4-dioxane, toluene, pyridine, DMF, DMSO, or the mixed solvent thereof; said base is selected from pyridine, potassium carbonate, sodium carbonate, sodium bicarbonate, potassium bicarbonate, triethylamine, N,N-diethyl isopropyl amine, N,N-dimethylamine pyridine, N-methylmorphine, or the combination thereof.

In one embodiment, compound B2 is prepared through the following method:

(i) in an inert solvent, condensing 3-fluoro-4-aminophenol with 1-chloro-4-isocyanato-2-(trifluoromethyl)benzene to form compound B2;

In one embodiment, said inert solvent includes (but is not limited to): dichloromethane, dichloroethane, acetonitrile, n-hexane, toluene, tetrahydrofuran, N,N-dimethylformamide, N,N-dimethylacetamide, N-methylpyrrolidone, dimethylsulfoxide, or the combination thereof.

In one embodiment, said base is selected from potassium tert-butoxide, sodium hydride, potassium hydride, potassium carbonate, cesium carbonate, potassium phosphate, potassium hydroxide, sodium hydroxide or the combination thereof.

In one embodiment, method (a) further includes conducting the reaction in the presence of a catalyst, wherein said catalyst is selected from cuprous iodide and proline; or cuprous iodide and pyridyl formic acid.

In one embodiment, each reaction is conducted at 0-200° C.

In one embodiment, the reaction time is 0.2-72 h, preferably is 0.5-64 h, and more preferably is 1-48 h.

In the third aspect, the invention provides a method for preparing 4-chloro-N-(methyl-$d_3$)picolinamide, comprising:

(a1) in a basic condition and in an inert solvent, reacting methyl 4-chloropicolinate with (methyl-$d_3$)amine or salts thereof to form 4-chloro-N-(methyl-$d_3$)picolinamide; or (a2) in an inert solvent, reacting 4-chloropicolinoyl chloride with (methyl-d₃)amine to form 4-chloro-N-(methyl-d₃)picolinamide.

In one embodiment, said inert solvent includes tetrahydrofuran, ethanol, methanol, water, or the mixed solvent thereof.

In one embodiment, in steps (a1) and (a2), the reaction temperature is −10° C. to reflux temperature, preferably is −4° C. to 60° C., and more preferably is 5-50° C.

In one embodiment, in steps (a1) and (a2), the reaction time is 0.5-72 h, preferably is 1-64 h, and more preferably is 2-48 h.

In one embodiment, in step (a1), said basic condition means that potassium carbonate, sodium carbonate, cesium carbonate, sodium hydroxide, potassium hydroxide or the combination thereof is present in the reaction.

In the fourth aspect, the invention provides an intermediate of formula B2,

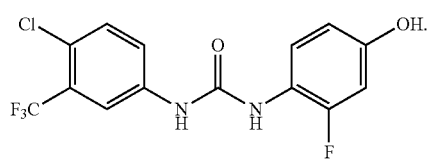

In the fifth aspect, the invention provides a method for preparing compound B2, comprising: in an inert solvent, condensing 3-fluoro-4-aminophenol with 1-chloro-4-isocyanato-2-(trifluoromethyl)benzene to form compound B2:

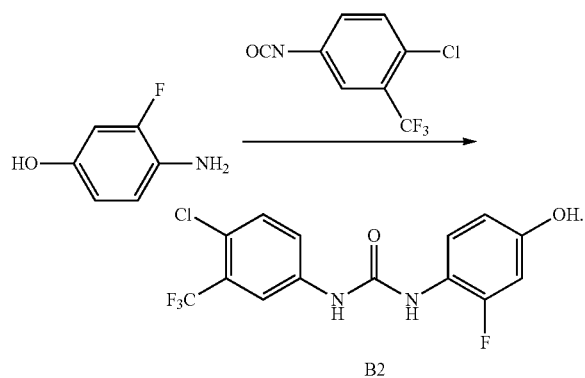

In the sixth aspect, the invention provides the use of the intermediate according to the first aspect or the fourth aspect of the invention for preparing deuterated diphenylurea or as the raw material for preparing deuterated diphenylurea.

In one embodiment, said deuterated diphenylurea includes
4-(4-(3-(4-chloro-3-(trifluoromethyl)phenyl]ureido)-3-fluoro-phenoxy)-N-(methyl-d₃)picolinamide CM4309;
4-(4-(3-(4-chloro-3-(trifluoromethyl)phenyl]ureido)-3-fluorophenoxy)-2-((methyl-d₃)carbamoyl)pyridine-1-oxide;
4-(4-(3-(4-chloro-3-(trifluoromethyl)phenyl]ureido)-3-fluorophenoxy)-N-(methyl-d₃)picolinamide p-toluenesulfonate (CM4309.TsOH);
4-(4-(3-(4-chloro-3-(trifluoromethyl)phenyl]ureido)-3-fluorophenoxy)-N-(methyl-d₃)picolinamide hydrochloride; or
4-(4-(3-(4-chloro-3-(trifluoromethyl)phenyl]ureido)-3-fluorophenoxy)-N-(methyl-d₃)picolinamide methanesulfonate ethanol complex.

In the seventh aspect, the invention provides the use of the following compound (CM4309) for preparing a pharmaceutical composition with inhibition of phosphokinases (such as raf kinases).

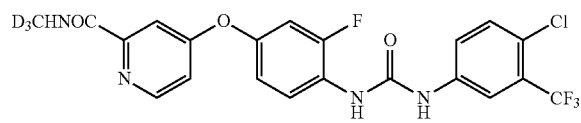

In one embodiment, said pharmaceutical composition can be used to prevent or treat the following diseases: cancer, cardiovascular diseases, inflammation, immunological diseases, nephrosis, angiogenesis, or prostatosis.

In one embodiment, said cancer includes (but is not limited to): non-small-cell lung cancer, uterine cancer, rectal cancer, cerebral cancer, head and neck cancer, bladder cancer, prostate cancer, breast cancer, solid tumor, kidney cancer, leukaemia, liver cancer, gastric cancer, or pancreatic cancer.

In the eighth aspect, the invention provides a treating method, comprising the step: administrating compound CM4309 of the invention to a subject in need of, or the crystal form, pharmaceutically acceptable salts, hydrates or solvates thereof, or administrating a pharmaceutical composition containing said compound, thereby inhibiting phosphokinases (such as raf kinases). Preferably, said disease includes cancer, cardiovascular disease, inflammation, immunological diseases, nephrosis, angiogenesis, or prostatosis.

It should be understood that in the present invention, any of the technical features specifically described above and below (such as in the Examples) can be combined with each other, thereby constituting new or preferred technical solutions that are not described one by one in the specification.

DESCRIPTION OF FIGURES

FIG. 1 shows inhibition efficacy of CM4306, CM4308 and CM4309 in nude mice xenograft model inoculated with human liver cancer cell SMMC-7721 (Mean±SEM). In this FIGURE, "treatment" means that the treating period was 14 days. "Control" means the blank control.

DETAILED DESCRIPTION OF INVENTION

After studies, the inventors unexpectedly discovered that the fluoro-substituted deuterated ω-diphenylurea of the invention and the pharmaceutically acceptable salts thereof possessed superior pharmacokinetics and/or pharmacodynamic properties compared with the un-deuterated compound. Therefore, they are much more suitable as raf kinase inhibitors for preparing medicaments for treating cancer and the relevant diseases. Moreover, the inventors further found that high purity diphenylurea compounds could be high efficiently and readily prepared by using a new intermediate of formula V or B2. Based on this discovery, the inventors completed the present invention.

DEFINITION

As used herein, the term "halogen" refers to F, Cl, Br and I. Preferably, halogen is selected from F, Cl, or Br.

As used herein, the term "alkyl" refers to straight-chain or branched chain alkyl. Preferably, alkyl is C1-C4 alkyl, such as methyl, ethyl, propyl, iso-propyl, butyl, iso-butyl, tert-butyl and so on.

As used herein, the term "deuterated" means that one or more hydrogen in a compound or group is substituted by deuterium. "Deuterated" can be mono-substituted, bi-substituted, multi-substituted or total-substituted. The terms "one or more deuterium-substituted" and "substituted by deuterium once or more times" can be used interchangeably.

In one embodiment, the deuterium content at a deuterium-substituted position is at least greater than the natural abundance of deuterium (0.015%), preferably >50%, more preferably >75%, more preferably >95%, more preferably >97%, more preferably >99%, more preferably >99.5%.

In one embodiment, the compound of formula (I) comprises at least one deuterium atom, preferably three deuterium atoms, and more preferably five deuterium atoms.

As used herein, the term "compound CM4306" is 4-(4-(3-(4-chloro-3-(trifluoromethyl)phenyl]ureido)-phenoxy)-(N-methyl)picolinamide.

As used herein, the term "compound CM4308" is 4-(4-(3-(4-chloro-3-(trifluoromethyl)phenyl]ureido)-3-fluorophenoxy)-N-methylpicolinamide.

As used herein, the term "compound CM4309" is 4-(4-(3-(4-chloro-3-(trifluoromethyl)phenyl]ureido)-3-fluorophenoxy)-N-(methyl-d$_3$)picolinamide.

As used herein, the term "TsOH" represents p-toluenesulfonic acid. CM4309.TsOH represents the p-toluenesulfonate of CM4309.

Deuterium-Substituted ω-Diphenylurea

The preferred deuterated ω-diphenylurea compound of the invention is as formula (I):

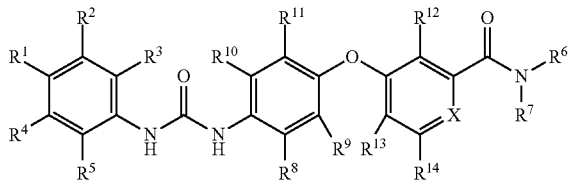

(I)

wherein,

X is N or N$^+$—O$^-$;

R$^1$ is halogen (such as F, Cl or Br), one or more deuterium-substituted or perdeuterated C1-C4 alkyl;

R$^2$ is non-deuterated C1-C4 alkyl, one or more deuterium-substituted or perdeuterated C1-C4 alkyl, or partly or totally halogen-substituted C1-C4 alkyl;

each of R$^3$, R$^4$, R$^5$, R$^8$, R$^9$, R$^{10}$, R$^{11}$, R$^{12}$, R$^{13}$, and R$^{14}$ is independently hydrogen, deuterium, or halogen (such as F, Cl or Br);

R$^6$ is hydrogen, deuterium, or one or more deuterium-substituted or perdeuterated C1-C4 alkyl;

R$^7$ is hydrogen, deuterium, or one or more deuterium-substituted or perdeuterated C1-C4 alkyl; and provided that at least one of R$^2$, R$^3$, R$^4$, R$^5$, R$^6$, R$^7$, R$^8$, R$^9$, R$^{10}$, R$^{11}$, R$^{12}$, R$^{13}$ or R$^{14}$ is deuterated or is deuterium.

In one embodiment, the deuterium content at a deuterium-substituted position is at least greater than the natural abundance of deuterium (0.015%), preferably >30%, more preferably >50%, more preferably >75%, or >95%, or >99%.

In one embodiment, except for H, all or nearly all (>99 wt %) of the elements (such as N, C, O, F, etc.) of compound (I) are naturally existing elements with highest abundance, such as $^{14}$N, $^{12}$C, $^{16}$O and $^{19}$F.

In one embodiment, compounds of formula (I) contain at least one deuterium atom, preferably three deuterium atoms, and more preferably five deuterium atoms.

In one embodiment, R$^1$ is halogen, and preferably chlorine.

In one embodiment, R$^2$ is trifluoromethyl.

In one embodiment, R$^6$ or R$^7$ is independently selected from hydrogen, deuterium, deuterated methyl, or deuterated ethyl; preferably, mono-deuterated methyl, bi-deuterated methyl, tri-deuterated methyl, mono-deuterated ethyl, bi-deuterated ethyl, tri-deuterated ethyl, tetra-deuterated ethyl, or penta-deuterated ethyl.

In one embodiment, R$^6$ or R$^7$ is independently selected from hydrogen, methyl or tri-deuterated methyl.

In one embodiment, R$^3$, R$^4$ or R$^5$ is independently selected from hydrogen or deuterium.

In one embodiment, R$^8$, R$^9$, R$^{10}$ or R$^{11}$ is independently selected from hydrogen or deuterium.

In one embodiment, R$^{12}$, R$^{13}$ or R$^{14}$ is independently selected from hydrogen or deuterium.

In one embodiment, said compounds are selected from:

4-(4-(3-(4-chloro-3-(trifluoromethyl)phenyl)ureido)phenoxy)-N-(methyl-d$_3$)picolinamide (or N-(4-chloro-3-(trifluoromethyl)phenyl)-N'-(4-(2-(N-(methyl-d$_3$)aminoformyl)-4-pyridyloxy)phenyl)urea);

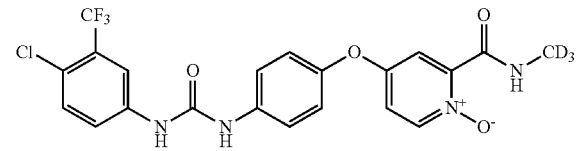 [SMILES: [2H]C([2H])([2H])NC(=O)c1cc(Oc2ccc(NC(=O)Nc3ccc(Cl)c(C(F)(F)F)c3)cc2)cc[n+]1[O-]]

4-(4-(3-(4-chloro-3-(trifluoromethyl)phenyl)ureido)phenoxy)-N-(methyl-d$_3$)aminoformyl)pyridine-1-oxide;

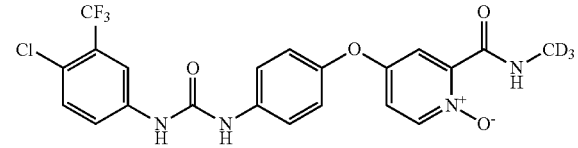 [SMILES: [2H]C([2H])([2H])NC(=O)c1cc(Oc2ccc(NC(=O)Nc3ccc(Cl)c(C(F)(F)F)c3)cc2)cc[n+]1[O-]]

4-(4-(3-(4-chloro-3-(trifluoromethyl)phenyl]ureido)-3-fluorophenoxy)-N-(methyl-d$_3$)picolinamide (or N-(4-chloro-3-(trifluoromethyl)phenyl)-N'-(4-(2-(N-(methyl-d$_3$)aminoformyl)-4-pyridyloxy)-3-fluoro-phenyl)urea);

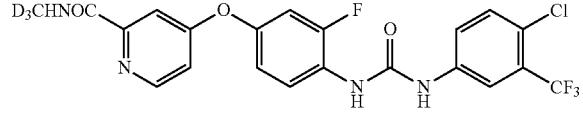

4-(4-(3-(4-chloro-3-(trifluoromethyl)phenyl)ureido)-3-fluorophenoxy)-2-((methyl-d$_3$)carbamoyl)pyridine-1-oxide;

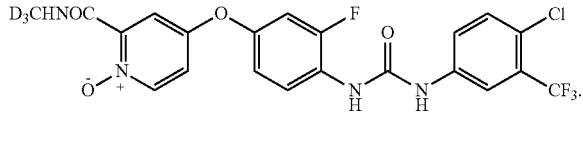

Intermediates

As used herein, the term "the intermediate of the invention" is compound V or compound B' (especially compound B2).

Except for H, all or nearly all (>99 wt %) of the elements (such as N, C, O, etc.) of compound (I) are naturally existing elements with highest abundance, such as $^{14}N$, $^{12}C$ and $^{16}O$.

Active Ingredients

As used herein, the term "compound of the invention" refers to the compound of formula (I). This term also includes various crystal forms, pharmaceutically acceptable salts, hydrates or solvates of the compound of formula (I).

The preferred compound is CM4309 or its pharmaceutically acceptable salts.

As used herein, the term "pharmaceutically acceptable salts" refers to the salts which are suitably used as medicaments and formed by the compound of the invention and acid or base. Pharmaceutically acceptable salts include inorganic salts and organic salts. A preferred salt is formed by the compound of the invention and acid. The acid suitable for forming salts includes, but is not limited to, inorganic acid, such as hydrochloric acid, hydrobromic acid, hydrofluoric acid, sulfuric acid, nitric acid, phosphoric acid; organic acid, such as formic acid, acetic acid, propionic acid, oxalic acid, malonic acid, succinic acid, fumaric acid, maleic acid, lactic acid, malic acid, tartaric acid, citric acid, picric acid, methanesulfonic acid, benzene methanesulfonic acid, benzene sulfonic acid; and acidic amino acid, such as aspartic acid, glutamic acid.

Preparation

The preparation methods of compound (I) and the novel intermediates are described in detail as below. However, these specific methods won't limit the invention. The compounds of the invention can be readily prepared by optionally combining any of the methods described in the specification with various methods known in the art, and such combination can be easily carried out by the skilled in the art.

The method for preparing un-deuterated w-diphenylurea and the physiologically compatible salts thereof used in the invention is known. The deuterated ω-diphenylurea can be prepared by the same route using the corresponding deuterated compounds as the starting materials. For example, compound (I) can be prepared according to the method described in WO2000/042012, except that the deuterated material is used instead of un-deuterated material in the reaction.

In general, during the preparation, each reaction is conducted in an inert solvent, at a temperature between room temperature to reflux temperature (such as 0-80° C., preferably 0-50° C.). Generally, the reaction time is 0.1-60 h, preferably, 0.5-48 h.

Taking CM4309 as an example, an optimized preparation route is shown as follows:

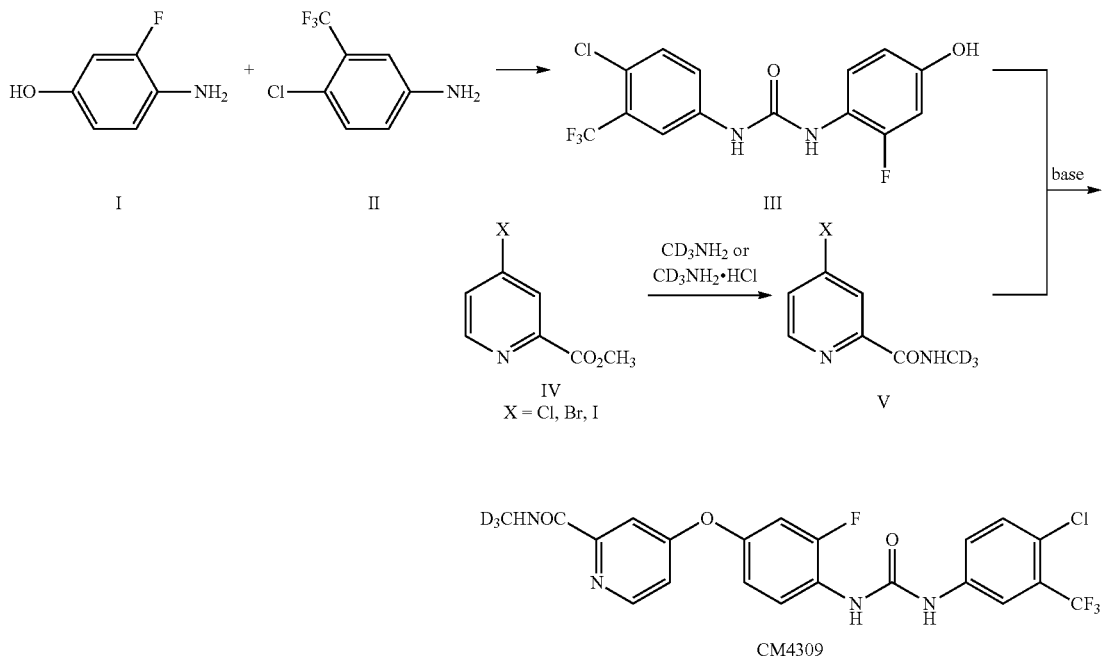

Scheme 1

As shown in Scheme 1, in the presence of N,N'-carbonyldiimidazole, phosgene or triphosgene, 3-fluoro-4-aminophenol (Compound I) reacts with 3-trifluoromethyl-4-chloroaniline (Compound II) to give 1-(4-chloro-3-(trifluoromethyl)phenyl)-3-(2-fluoro-hydroxyphenyl)urea (Compound III). N-(methyl-$d_3$)picolinamide (Compound V) is obtained by reacting methyl picolinate (Compound IV) with (methyl-$d_3$)amine or (methyl-$d_3$)amine hydrochloride directly or in the presence of a base, such as sodium carbonate, potassium carbonate, sodium hydroxide, triethylamine, pyridine and the like. In the presence of a base (such as potassium tert-butoxide, sodium hydride, potassium hydride, potassium carbonate, cesium carbonate, potassium phosphate, potassium hydroxide, sodium hydroxide) and an optional catalyst (such as cuprous iodide and proline, or cuprous iodide and picolinic acid), Compound III reacts with Compound V to form compound CM-4309. The above reactions are conducted in an inert solvent, such as dichloromethane, dichloroethane, acetonitrile, n-hexane, toluene, tetrahydrofuran, N,N-dimethylformamide, dimethyl sulfoxide and so on, and at a temperature of 0-200° C.

Taking CM4309 as an example, another preferred preparation route is shown as below:

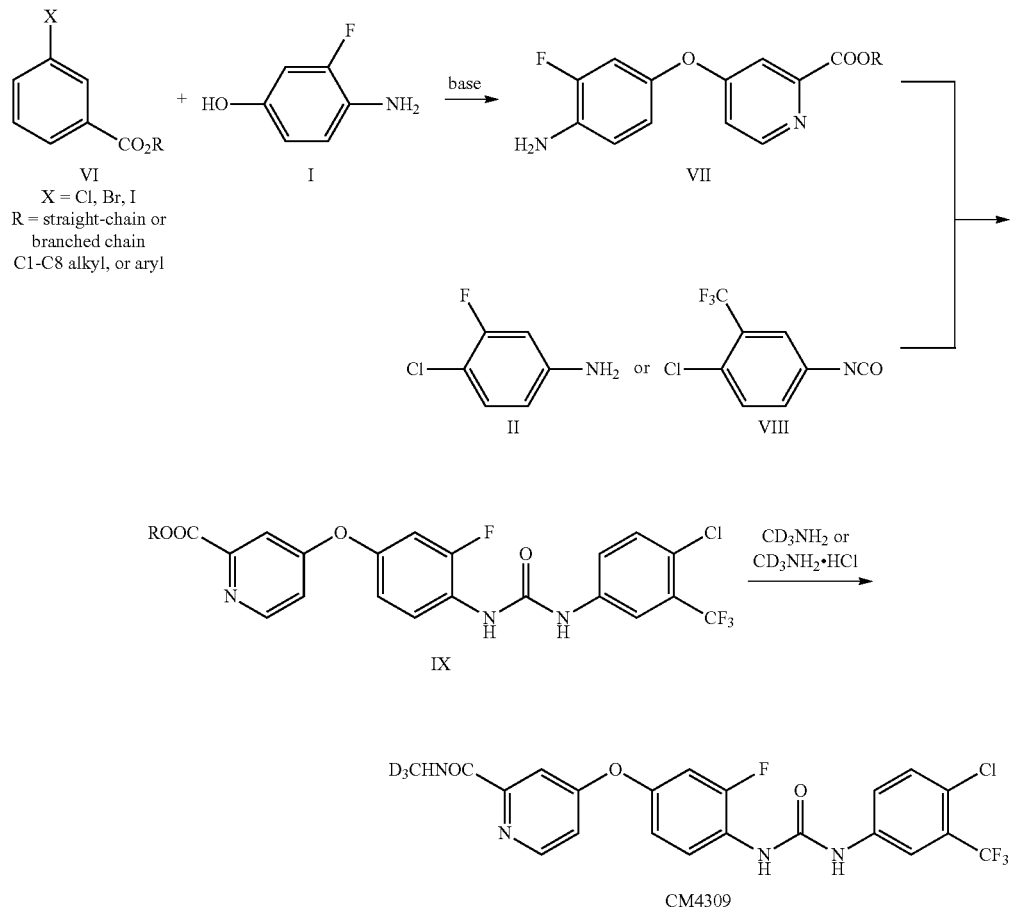

As shown in Scheme 2, amine (Compound VII) is obtained by reacting picolinate (Compound VI) with 3-fluoro-4-aminophenol (Compound I) in the presence of a base (such as potassium tert-butoxide, sodium hydride, potassium hydride, potassium carbonate, cesium carbonate, potassium phosphate, potassium hydroxide, sodium hydroxide) and an optional catalyst (such as cuprous iodide and proline, or cuprous iodide and pyridine carboxylic acid). The urea (Compound IX) is obtained by reacting Compound VII with Compound II in the presence of N,N'-carbonyldiimidazole, phosgene or triphosgene, or with 1-chloro-4-isocyanato-2-(trifluoromethyl)benzene (Compound VIII). Compound CM4309 is obtained by reacting Compound IX with (methyl-$d_3$)amine or (methyl-$d_3$)amine hydrochloride directly, or in the presence of a base (such as sodium carbonate, potassium carbonate, sodium hydroxide, triethylamine, pyridine and the like). The above reactions are conducted in an inert solvent, such as dichloromethane, dichloroethane, acetonitrile, n-hexane, toluene, tetrahydrofuran, N,N-dimethylformamide, dimethyl sulfoxide and so on, and at a temperature of 0-200° C.

Taking CM4309 as an example, another preferred preparation is shown as below:

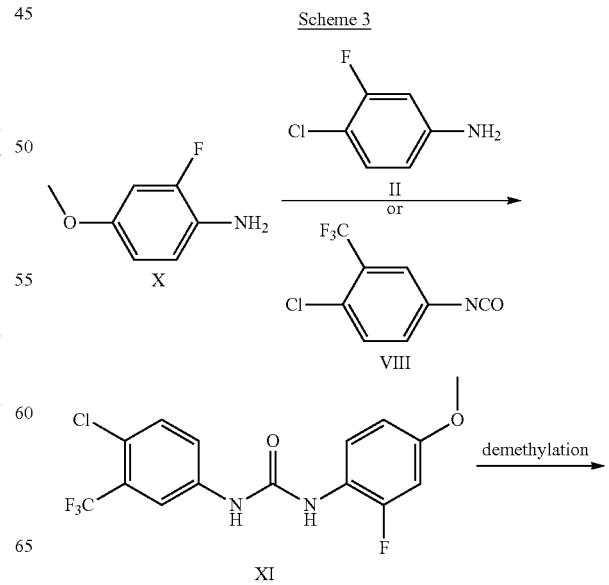

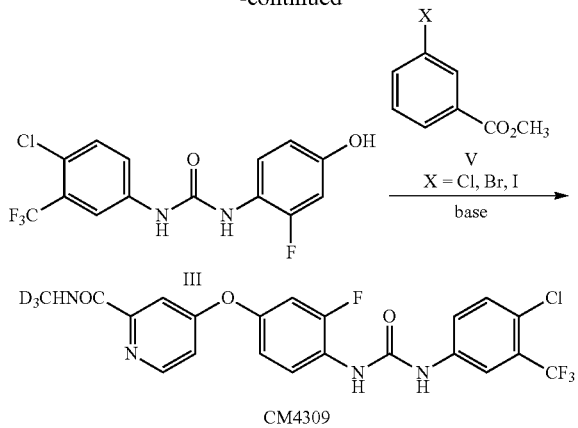

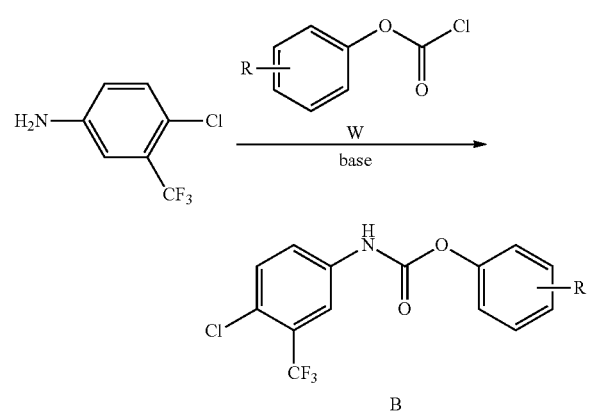

As shown in Scheme 3, the urea (Compound XI) is obtained by reacting 2-fluoro-4-methyloxyphenylamine (Compound X) with Compound II in the presence of N,N'-carbonyldiimidazole, phosgene or triphosgene, or with 1-chloro-4-isocyanato-2-(trifluoromethyl)benzene (Compound VIII). 1-(4-chloro-3-(trifluoromethyl)phenyl)-3-(2-fluoro-4-hydroxyphenyl)urea (Compound III) is obtained using any of demethylation methods known in the art. Compound CM4309 is obtained by reacting Compound III with Compound V by the same method as described in Scheme 1, or any methods known in the art. The above reactions are conducted in an inert solvent, such as dichloromethane, dichloroethane, acetonitrile, n-hexane, toluene, tetrahydrofuran, N,N-dimethylformamide, dimethyl sulfoxide and so on, and at a temperature of 0-200° C.

Taking CM4309 as an example, another preferred preparation is shown as below:

As shown in Scheme 4, 4-(4-amino-3-fluorophenoxy)-N-(methyl-d$_3$)picolinamide (compound B1) is obtained by reacting compound V and compound 3-fluoro-4-amino-phenol in an inert solvent and in a basic condition. In an inert solvent, compound M is obtained by reacting compound B1 with compound W; and in an inert solvent, compound CM4309 is obtained by reacting compound M with 4-chloro-3-trifluoromethyl-aniline. The above reactions are conducted in an inert solvent, such as dichloromethane, dichloroethane, acetonitrile, n-hexane, toluene, tetrahydrofuran, N,N-dimethylformamide, dimethyl sulfoxide and so on, and at a temperature of 0-200° C.

Taking CM4309 as an example, another preferred preparation is shown as below:

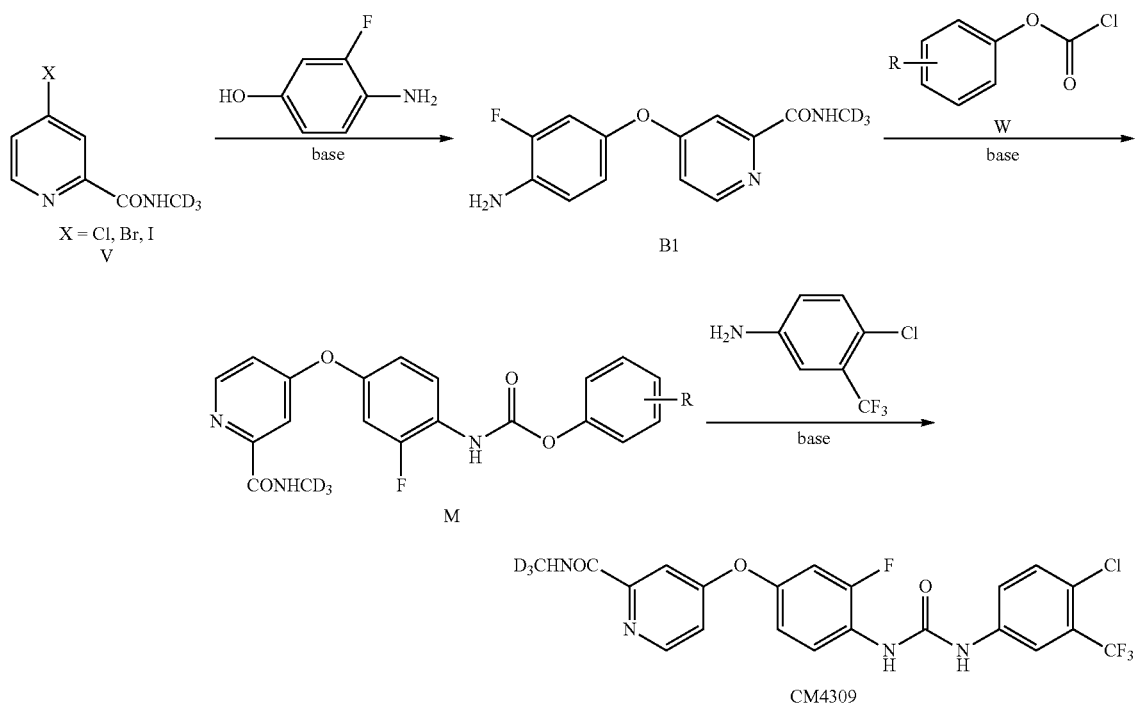

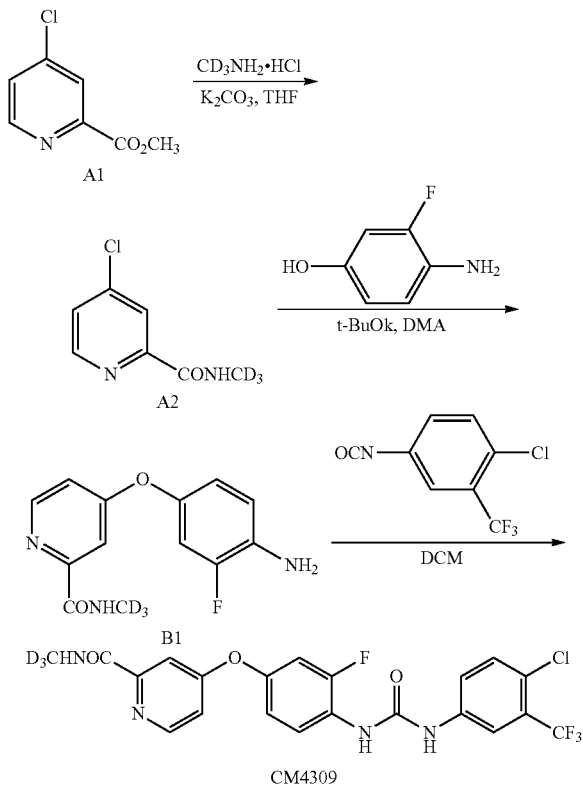

As shown in Scheme 5, compound B is obtained by reacting compound W and 4-chloro-3-trifluoromethyl-aniline in a basic condition. In a basic condition, compound CM4309 is obtained by reacting compound B1 with compound B. The above reactions are conducted in an inert solvent, such as dichloromethane, dichloroethane, acetonitrile, n-hexane, toluene, tetrahydrofuran, N,N-dimethylformamide, dimethyl sulfoxide and so on, and at a temperature of 0-200° C.

Taking CM4309 as an example, another preferred preparation is shown as below:

The deuterium can be introduced by using deuterated methylamine.

Alternatively, deuterated methylamine or the hydrochloride thereof can be prepared through the following reactions. Deuterated nitromethane is obtained by reacting nitromethane with deuterium water in the presence of a base (such as sodium hydride, potassium hydride, deuterated sodium hydroxide, deuterated potassium hydroxide, potassium carbonate and the like) or phase-transfer catalyst. The above experiment can be repeated if necessary to produce high purity of deuterated nitromethane. Deuterated nitromethane is reduced in the presence of zinc powder, magnesium powder, iron, or nickel and the like to form deuterated methylamine or the hydrochloride thereof.

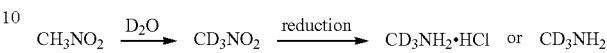

Furthermore, deuterated methylamine or the hydrochloride thereof can be obtained through the following reactions.

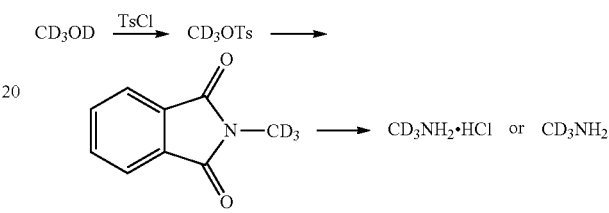

The key intermediate 3 can be synthesized from deuterium methanol through the following reactions.

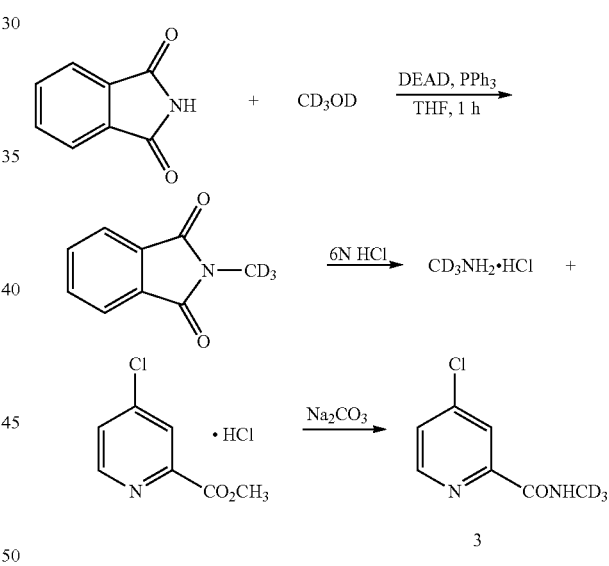

The detailed preparation procedure is described in Example 1.

The main advantages of the present invention include:

(1) Compounds of the invention possess excellent inhibition activity to phosphokinases, such as raf kinases.

(2) Various deuterated diphenylurea with high purity can be prepared readily and with high efficiency from formula V, formula B or formula B2.

(3) The reaction condition is milder and the operation process is safer.

The present invention will be further illustrated below with reference to the specific examples. It should be understood that these examples are only to illustrate the invention, not to limit the scope of the invention. The experimental methods with no specific conditions described in the following examples are generally performed under the conventional conditions, or according to the manufacture's instructions. Unless indicated otherwise, parts and percentage are calculated by weight.

Example 1

Preparation of N-(4-chloro-3-(trifluoromethyl)phenyl)-N'-(4-(2-(N-(methyl-d₃)aminoformyl)-4-pyridyloxy)phenyl)urea (Compound CM4307)

Route:

Scheme 7

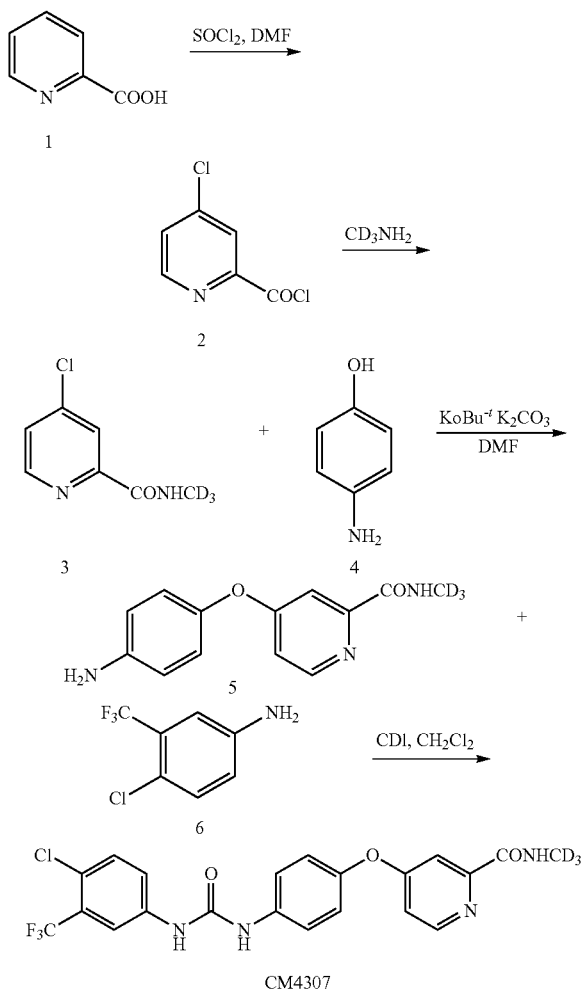

1. Preparation of 4-chloropyridyl-2-(N-(methyl-d₃))carboxamide (3)

Thionyl chloride (60 mL) was added into a 250 mL single-neck round-bottom flask equipped with waste gas treatment device. Anhydrous DMF (2 mL) was dropwise added slowly while keeping the temperature at 40-50° C. After addition, the mixture was stirred for 10 min, and then nicotinic acid (20 g, 162.6 mmol) was added in portions in 20 min. The color of the solution gradually changed from green into light purple. The reaction mixture was heated to 72° C., and refluxed for 16 h with agitation. A great amount of solid precipitated. The mixture was cooled to room temperature, diluted with toluene (100 mL) and concentrated to almost dry. The residue was diluted with toluene again and concentrated to dry. The residue was filtered and washed with toluene to give 4-chloropicolinoyl chloride as a light yellow solid. The solid was slowly added into a saturated solution of (methyl-d₃)amine in tetrahydrofuran in an ice-bath. The mixture was kept below 5° C. and stirred for 5 h. Then, the mixture was concentrated and ethyl acetate was added to precipitate a white solid. The mixture was filtered, and the filtrate was washed with saturated brine, dried over sodium sulfate and concentrated to give 4-chloropyridine-2-(N-(methyl-d₃))carboxamide (3) (20.68 g, 73% yield) as a light yellow solid.

$^1$H NMR (CDCl$_3$, 300 MHz): 8.37 (d, 1H), 8.13 (s, 1H), 7.96 (br, 1H), 7.37 (d, 1H).

2. Preparation of 4-(4-aminophenoxy)-2-pyridine-(N-(methyl-d₃))carboxamide (5)

To dry DMF (100 mL), 4-aminophenol (9.54 g, 0.087 mol) and potassium tert-butoxide (10.3 g, 0.092 mol) was added in turn. The color of the solution turned into deep brown. After stirring at room temperature for 2 h, 4-chloro-(N-(methyl-d₃))pyridine-2-carboxamide (3) (13.68 g, 0.079 mol) and anhydrous potassium carbonate (6.5 g, 0.0467 mol) were added, and then the reaction mixture was warmed up to 80° C. and stirred over night. TLC detection showed the reaction was complete. The reaction mixture was cooled to room temperature, and poured into a mixed solution of ethyl acetate (150 mL) and saturated brine (150 mL). The mixture was stirred and then stood for separation. The aqueous phase was extracted with ethyl acetate (3×100 mL). The extracted layers were combined, washed with saturated brine (3×100 mL) prior to drying over anhydrous sodium sulfate, and concentrated to afford 4-(4-aminophenoxy)-2-pyridine-(N-(methyl-d₃))carboxamide (18.00 g, 92% yield) as a light yellow solid.

$^1$H NMR (CDCl$_3$, 300 MHz): 8.32 (d, 1H), 7.99 (br, 1H), 7.66 (s, 1H), 6.91-6.85 (m, 3H), 6.69 (m, 2H), 3.70 (br, s, 2H).

3. Preparation of N-(4-chloro-3-(trifluoromethyl)phenyl)-N'-(4-(2-(N-(methyl-d₃)aminoformyl)-4-pyridyloxy)phenyl)urea (CM4307)

To methylene chloride (120 mL), 4-chloro-3-trifluoromethyl-phenylamine (15.39 g, 78.69 mmol) and N,N'-carbonyldiimidazole (13.55 g, 83.6 mmol) were added. After stirring at room temperature for 16 h, a solution of 4-(4-aminophenoxy)-2-pyridine-(N-(methyl-d₃))carboxamide (18 g, 73 mmol) in methylene chloride (180 mL) was slowly added dropwise, and the reaction mixture was stirred at room temperature for another 18 h. TLC detection showed the reaction was complete. The mixture was concentrated to about 100 mL by removing methylene chloride through a rotary evaporator and stood for several h at room temperature. A great amount of white solid precipitated. The suspension was filtered and the solid was washed with abundant methylene chloride. The filtrate was concentrated by removing some solvents, and some solid precipitated again. Two parts of solid were combined and washed with abundant methylene chloride to afford N-(4-chloro-3-(trifluoromethyl)phenyl)-N'-(4-(2-(N-(methyl-d₃)aminoformyl)-4-pyridyloxy)phenyl)urea (CM4307, 20.04 g, 58% yield) as a white powder (pure product).

$^1$H NMR (CD$_3$OD, 300 MHz): 8.48 (d, 1H), 8.00 (d, 1H), 7.55 (m, 5H), 7.12 (d, 1H), 7.08 (s, 2H), ESI-HRMS m/z: C$_{21}$H$_{13}$D$_3$ClF$_3$N$_4$O$_3$, Calcd. 467.11, Found 490.07 (M+Na)$^+$.

Furthermore, Compound CM4307 was dissolved in methylene chloride and reacted with benzoperoxoic acid to afford the oxidized derivative: 4-(4-(3-(4-chloro-3-(trifluoromethyl)phenyl)ureido)phenoxy)-2-(N-(methyl-d₃)aminoformyl)pyridine-1-oxide.

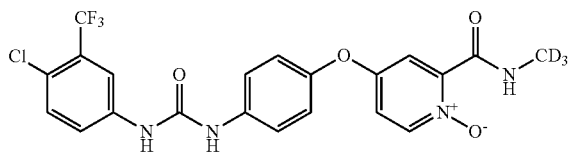 [SMILES: [2H]C([2H])([2H])NC(=O)c1cc(Oc2ccc(NC(=O)Nc3ccc(Cl)c(C(F)(F)F)c3)cc2)cc[n+]1[O-]]

Example 2

Preparation of CM4309 based on 4-chloro-N-(methyl-d₃)picolinamide (the intermediate A2)

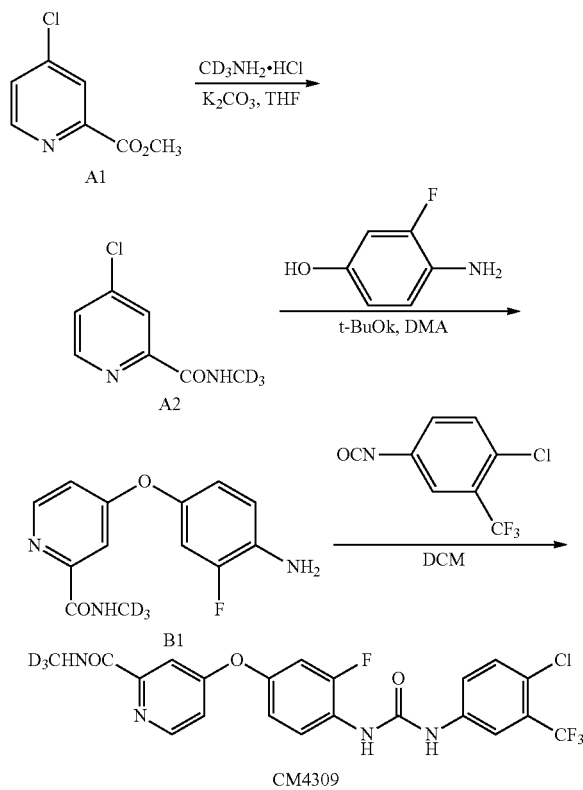

1. Preparation of 4-chloro-N-(methyl-d₃)picolinamide (intermediate A2)

Method 1:

Into a three-necked bottom flask with tetrahydrofuran (250 mL), methyl 4-chloro-2-picolinate (50 g, 291 mmol, 1 eq) was added. N-(methyl-d₃)amine hydrochloride (31 g, 437 mmol, 1.5 eq), anhydrous potassium carbonate (80 g, 583 mmol, 2 eq) were added with stirring. After the mixture was stirred at room temperature for 20 h, water (250 mL) and methyl tert-butyl ether (150 mL) were added. The mixture was stirred and separated to obtain the organic phase. The aqueous layer was extracted with methyl tert-butyl ether (100 mL). The organic phases were combined, dried over anhydrous sodium sulfate and filtered. The solvent in the filtrate was removed under reduced pressure to give the title compound (48 g, purity 99%, yield 96%) as a light yellow oily liquid.

¹H NMR (DMSO-d₆, 400 MHz): δ7.64 (dd, J=2 Hz, 5.2 Hz, 1H), 7.97 (d, J=1.6 Hz, 1H), 8.54 (d, J=5.2 Hz, 1H), 8.74 (br, 1H).

MS (ESI, m/z) calcd. for $C_7H_4D_3ClN_2O$: 173, found: 174 $[M+H]^+$

Method 2:

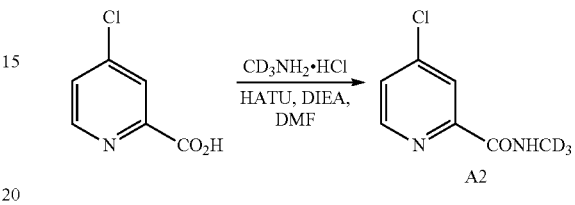

4-chloropicolinic acid (200 mg, 1.27 mmol, 1 eq) was dissolved in N,N-dimethylformide (DMF, 5 mL). (N-(methyl-d₃))amine hydrochloride (179 mg, 2.54 mmol, 2 eq), 2-(7-aza-1H-benzotriazole-1-yl)-1,1,3,3-tetramethyluronium hexafluorophosphate (HATU, 965 mg, 2.54 mmol, 2 eq) and N,N-diisopropylethylamine (DIEA, 492 mg, 3.81 mmol, 3 eq) were added. The resulted mixture was stirred at room temperature for 16 h. Water (20 mL) was added, and the resulted mixture was extracted with ethyl acetate (30 mL). The organic phase was washed with saturated brine (10 mL×3), dried over anhydrous sodium sulfate. The solvent in the filtrate was removed under reduced pressure to give the title compound (200 mg, purity 97%, yield 91%) as a light yellow liquid.

¹H NMR (DMSO-d₆, 400 MHz): δ7.64 (dd, J=2 Hz, 5.2 Hz, 1H), 7.97 (d, J=1.6 Hz, 1H), 8.54 (d, J=5.2 Hz, 1H), 8.74 (br, 1H).

MS (ESI, m/z) calcd. for $C_7H_4D_3ClN_2O$: 173, found: 174 $[M+H]^+$

2. Preparation of 4-(4-amino-3-fluorophenoxy)-N-(methyl-d₃)picolinamide B1

To N,N-dimethylacetylamide (DMA, 50 mL), potassium tert-butoxide (15 g, 130 mmol, 1.3 eq) was added. At 0-5° C., a solution of 3-fluoro-4-aminophenol (16 g, 127 mmol, 1.3 eq) in DMA (50 mL) was slowly added dropwise and the mixture was stirred at room temperature for 20 min. The mixture was heated to 100° C. and a solution of 4-chloro-N-(methyl-d₃)picolinamide A2 (17 g, 97 mmol, 1 eq) in DMA (50 mL) was slowly added dropwise. After the addition, the mixture was stirred for another 0.5 h, then cooled to room temperature, diluted with ethyl acetate (1.5 L) and stirred for 0.5 h. Then the mixture was filtered to remove the inorganic salt. The filtrate was washed with water (500 mL×3), dried over anhydrous sodium sulfate and concentrated under reduced pressure to remove the solvent. Ethanol (100 mL) was added into the resulted crude product (100 mL). The mixture was refluxed for 2 h with agitation, then cooled to room temperature and filtered to give the title compound (20 g, HPLC purity 96%, yield 80%) as a brown solid.

¹H NMR (CD₃OD, 400 MHz): δ6.74-6.77 (m, 1H), 6.87 (dd, J=2.4 Hz, 11.6 Hz, 1H), 6.93 (t, J=10 Hz, 1H), 7.02 (dd, J=2.8 Hz, 6 Hz, 1H), 7.54 (d, J=2.4 Hz, 1H), 8.44 (d, J=6 Hz, 1H).

MS (ESI, m/z) calcd. for $C_{13}H_9D_3ClN_3O_2$: 264, found: 265$[M+H]^+$

3. Preparation of 4-(4-(3-(4-chloro-3-(trifluoromethyl)phenyl]ureido)-3-fluorophenoxy)-N-(methyl-d₃)picolinamide (CM4309)

Method 1:

At room temperature, 1-chloro-4-isocyanato-2-(trifluoromethyl)benzene (13 g, 58 mmol, 1.1 eq) was added into a single-necked bottom flask with dichloromethane (70 mL). A solution of 4-(4-amino-3-fluorophenoxy)-N-(methyl-d₃)picolinamide (14 g, 53 mmol, 1 eq) in dichloromethane (350 mL) was slowly added dropwise to the above solution and the resulted mixture was stirred at room temperature for 20 h. After the reaction was complete, the mixture was filtered and the product was washed with dichloromethane (20 mL×2) to give a light brown solid (13 g, purity 98%, yield 50%).

$^1$H NMR (DMSO-d₆, 400 MHz): δ 7.06-7.10 (m, 1H), 7.19 (dd, J=2.4 Hz, 5.6 Hz, 1H), 7.35 (dd, J=2.8 Hz, 12 Hz, 1H), 7.43 (d, J=2.4 Hz, 1H), 7.63 (m, 2H), 8.14 (br, 1H), 8.17 (t, J=8.8 Hz, 1H), 8.53 (d, J=5.6 Hz, 1H), 8.75 (d, J=1.6 Hz, 1H), 8.78 (br, 1H), 9.54 (br, 1H).

MS (ESI, m/z) calcd. for $C_{21}H_{12}D_3ClF_4N_4O_3$: 485, found: 486 [M+H]⁺

Method 2:

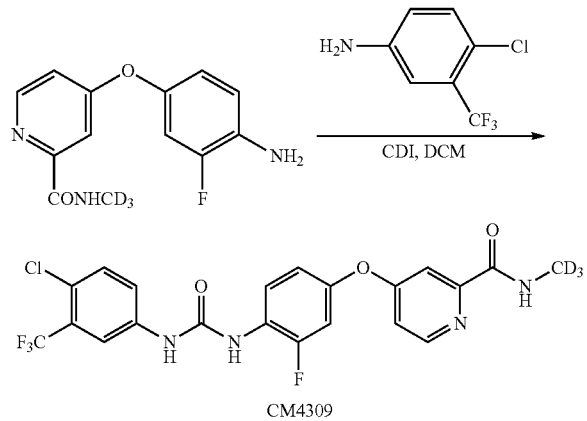

At room temperature, 4-chloro-3-trifluoromethyl-aniline (300 mg, 1.53 mmol, 1.05 eq) was dissolved in dichloromethane (5 mL). N,N-carbonyldiimidazole (CDI, 265 mg, 1.64 mmol, 1.12 eq) was added and the resulted mixture was stirred at room temperature for 16 h. To the above reaction mixture, 4-(4-amino-3-fluorophenoxy)-N-(methyl-d₃)picolinamide (386 mg, 1.46 mmol, 1 eq) was added. The mixture was stirred at room temperature for 20 h. The solvent was removed under reduced pressure. Petroleum ether (10 mL) and ethyl acetate (5 mL) were added and the resulted mixture was refluxed for 2 h. The mixture was cooled to room temperature and filtered to give CM4309 (635 mg, purity 95%, yield 90%) as a light brown solid.

$^1$H NMR (DMSO-d₆, 400 MHz): δ 7.06-7.10 (m, 1H), 7.19 (dd, J=2.4 Hz, 5.6 Hz, 1H), 7.35 (dd, J=2.8 Hz, 12 Hz, 1H), 7.43 (d, J=2.4 Hz, 1H), 7.63 (m, 2H), 8.14 (br, 1H), 8.17 (t, J=8.8 Hz, 1H), 8.53 (d, J=5.6 Hz, 1H), 8.75 (d, J=1.6 Hz, 1H), 8.78 (br, 1H), 9.54 (br, 1H).

MS (ESI, m/z) calcd. for $C_{21}H_{12}D_3ClF_4N_4O_3$: 485, found: 486 [M+H]⁺

Example 3

Preparation of CM4309 based on 4-chloro-N-(methyl-d₃)picolinamide (the intermediate A2)

Preparation of 1-(4-chloro-3-trifluoromethyl-phenyl)-3-(2-fluoro-4-hydroxyl-phenyl)-urea B2

At room temperature, 3-fluoro-4-amino-phenol (500 mg, 3.93 mmol, 1 eq) was dissolved in N,N-dimethylformide (3 mL). A solution of 1-chloro-4-isocyanato-2-(trifluoromethyl)benzene (917 mg, 4.13 mmol, 1.05 eq) in dichloromethane (3 mL) was added dropwise. The resulted mixture was stirred at room temperature for 16 h. The mixture was added with water (10 mL) and extracted with ethyl acetate (20 mL). The organic phase was washed with saturated brine (10 mL×3), and dried over anhydrous sodium sulfate. The solvent in the organic phase was removed under reduced pressure, and the resulted solid was refluxed in petroleum ether (15 mL) and ethyl acetate (5 mL) for 2 h. The mixture was cooled to room temperature and filtered to give title compound (1.2 g, purity 98%, yield 89%) as a brown solid.

$^1$H NMR (DMSO-d₆, 400 MHz): δ 6.56-6.59 (m, 1H), 6.64 (dd, J=2.4 Hz, 12.4 Hz, 1H), 7.59-7.63 (m, 3H), 8.11 (br, 1H), 8.28 (br, 1H), 9.34 (br, 1H), 9.69 (br, 1H).

MS (ESI, m/z) calcd. for $C_{14}H_9ClF_4N_2O_2$: 348, found: 349 [M+H]⁺

Preparation of 4-(4-(3-(4-chloro-3-(trifluoromethyl)phenyl]ureido)-3-fluorophenoxy)-N-(methyl-d₃)picolinamide (CM4309)

Potassium tert-butoxide (906 mg, 8.09 mmol, 1.4 eq) was dissolved in N,N-dimethylacetamide (DMA, 5 mL). A solution of 1-(4-chloro-3-trifluoromethyl-phenyl)-3-(2-fluoro-4-hydroxy-phenyl)-urea (2.8 g, 8.09 mmol, 1.4 eq) in DMA (5 mL) was slowly added dropwise at 0° C. The resulted mixture was stirred at room temperature for 20 min. The mixture was heated to 100° C. and a solution of 4-chloro-N-(methyl-$d_3$) picolinamide (1 g, 5.78 mmol, 1 eq) in DMA (5 mL) was added dropwise. After the addition, the mixture was cooled to room temperature, diluted with ethyl acetate (200 mL) and stirred for 0.5 h, and then filtered to remove the inorganic salt. The filtrate was washed with water (5 mL×3), dried over anhydrous sodium sulfate and the solvent in the filtrate was removed under reduced pressure. The crude product was purified by column chromatography (petroleum ether: ethyl acetate=4:1) to give CM4309 (520 mg, purity 98%, yield 20%) as a brown solid.

$^1$H NMR (DMSO-$d_6$, 400 MHz): δ 7.06-7.10 (m, 1H), 7.19 (dd, J=2.4 Hz, 5.6 Hz, 1H), 7.35 (dd, J=2.8 Hz, 12 Hz, 1H), 7.43 (d, J=2.4 Hz, 1H), 7.63 (m, 2H), 8.14 (br, 1H), 8.17 (t, J=8.8 Hz, 1H), 8.53 (d, J=5.6 Hz, 1H), 8.75 (d, J=1.6 Hz, 1H), 8.78 (br, 1H), 9.54 (br, 1H).

MS (ESI, m/z) calcd. for $C_{21}H_{12}D_3ClF_4N_4O_3$: 485, found: 486 [M+H]$^+$ Example 4

Preparation of CM4309 based on 4-chloro-N-(methyl-$d_3$)picolinamide (the intermediate A2)

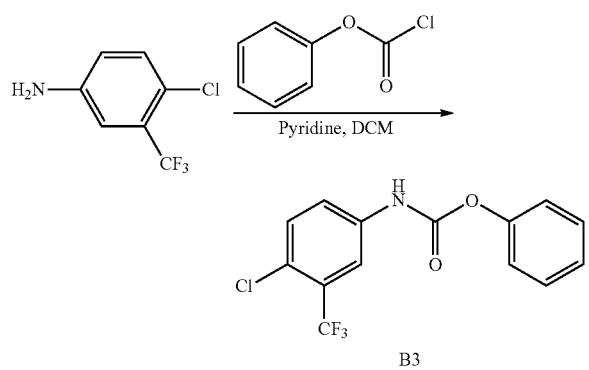

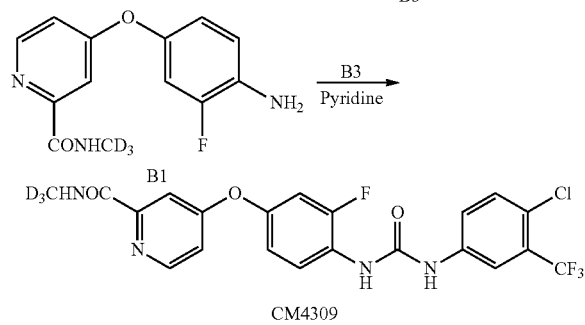

Preparation of phenyl 4-chloro-3-(trifluoromethyl)phenylcarbamate B3

At room temperature, 4-chloro-3-trifluoromethyl-aniline (4.9 g, 25 mmol, 1 eq) was dissolved in dichloromethane (50 mL). A solution of phenyl chloroformate (3.9 g, 25 mmol, 1 eq) in dichloromethane (10 mL) was added, and the mixture was stirred for 1 h at room temperature. Dilute hydrochloride (1 N, 50 mL) was added, and the mixture was washed with water (40 mL×3) and separated. The organic phase was dried over anhydrous sodium sulfate and filtered. The solvent in the filtrate was removed to give the title compound (7.5 g, purity 99%, yield 94%) as an off-white solid.

$^1$H NMR (DMSO-$d_6$, 400 MHz): δ 7.25-7.30 (m, 3H), 7.45 (t, J=8 Hz, 2H), 7.67-7.78 (m, 2H), 8.07 (d, J=2 Hz, 1H), 10.73 (br, 1H).

MS (ESI, m/z) calcd. for $C_{14}H_9ClF_3NO_2$: 315, found: 316 [M+H]$^+$

Preparation of 4-(4-(3-(4-chloro-3-(trifluoromethyl) phenyl]ureido)-3-fluorophenoxy)-N-(methyl-$d_3$) picolinamide CM4309

At room temperature, phenyl 4-chloro-3-(trifluoromethyl) phenylcarbamate (0.95 g, 3.0 mmol, 1 eq) was dissolved in pyridine (10 mL). 4-(4-amino-3-fluorophenoxy)-N-(methyl-$d_3$)picolinamide (0.79 g, 3.0 mmol, 1 eq) was added, and the mixture was heated to 85° C. and stirred for 2 h. The solvent was removed under reduced pressure and to the residue was added ethyl acetate (50 mL). The mixture was washed with dilute hydrochloride (1 N, 10 mL) and saturated brine (10 mL), and separated. The organic phase was dried over anhydrous sodium sulfate and filtered. The solvent in the filtrate was removed under reduced pressure. To the residue was added ethyl acetate (3 mL), and the mixture was stirred for 1 h and filtered to give the title compound (0.5 g, purity 96%, yield 35%) as an off-white solid.

$^1$H NMR (DMSO-$d_6$, 400 MHz): δ 7.06-7.10 (m, 1H), 7.19 (dd, J=2.4 Hz, 5.6 Hz, 1H), 7.35 (dd, J=2.8 Hz, 12 Hz, 1H), 7.43 (d, J=2.4 Hz, 1H), 7.63 (m, 2H), 8.14 (br, 1H), 8.17 (t, J=8.8 Hz, 1H), 8.53 (d, J=5.6 Hz, 1H), 8.75 (d, J=1.6 Hz, 1H), 8.78 (br, 1H), 9.54 (br, 1H).

MS (ESI, m/z) calcd. for $C_{21}H_{12}D_3ClF_4N_4O_3$: 485, found: 486 [M+H]$^+$ Example 5

Preparation of CM4309 based on 4-chloro-N-(methyl-$d_3$)picolinamide (the intermediate A2)

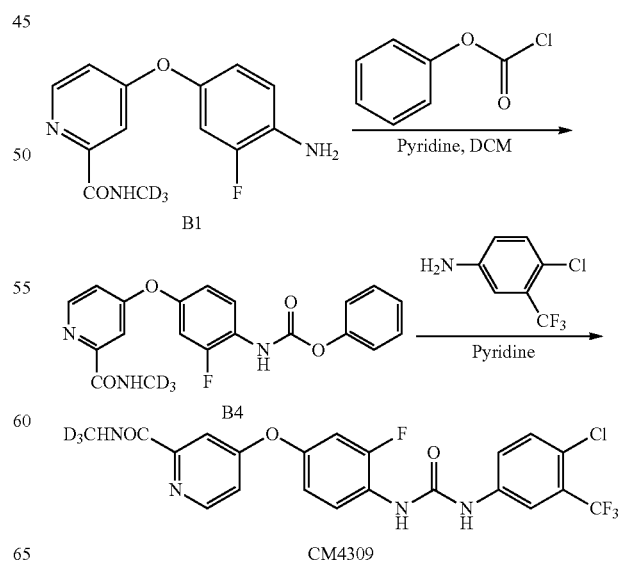

Preparation of phenyl 2-fluoro-4-(2-((methyl-d₃)carbamoyl)pyridin-4-yloxy)phenylcarbamate B4

4-(4-amino-3-fluorophenoxy)-N-(methyl-d₃)picolinamide (2.60 g, 10 mmol, 1 eq) was dissolved in dichloromethane (15 mL). Pyridine (1.58 g, 20 mmol, 2 eq) was added. A solution of phenyl chloroformate (1.88 g, 12 mmol, 1.2 eq) in dichloromethane (15 mL) was added at room temperature, and the mixture was stirred at room temperature for 1 h. The mixture was washed with dilute hydrochloride (1 N, 30 mL) and saturated brine (10 mL×2), and separated. The organic phase was dried over anhydrous sodium sulfate and filtered. The solvent in the filtrate was removed under reduced pressure to give the title compound (3.6 g, purity 95%, yield 94%).

¹H NMR (DMSO-d₆, 400 MHz): δ7.10-7.13 (m, 1H), 7.21 (dd, J=2.8 Hz, 5.6 Hz, 1H), 7.26 (t, J=6.4 Hz, 3H), 7.36 (dd, J=2.8 Hz, 11.6 Hz, 1H), 7.43-7.47 (m, 3H), 7.80 (t, J=8.4 Hz, 1H), 8.55 (d, J=5.2 Hz, 1H), 8.79 (br, 1H), 10.10 (br, 1H).

MS (ESI, m/z) calcd. for $C_{20}H_{13}D_3FN_3O_4$: 384, found: 385[M+H]⁺

Preparation of 4-(4-(3-(4-chloro-3-[(trifluoromethyl)phenyl]ureido)-3-fluorophenoxy)-N-(methyl-d₃) picolinamide CM4309

At room temperature, phenyl 2-fluoro-4-(2-((methyl-d₃)carbamoyl)pyridin-4-yloxy)phenylcarbamate (1.92 g, 5 mmol, 1 eq) was dissolved in pyridine (10 mL). 4-chloro-3-trifluoromethyl aniline (0.98 g, 5 mmol, 1 eq) was added. The mixture was heated to 85° C. and stirred for 2 h. The solvent was removed under reduced pressure followed by addition of ethyl acetate (100 mL). The resulted mixture was washed with saturated brine (30 mL×3) and separated. The organic phase was dried over anhydrous sodium sulfate, and filtered. The solvent in the filtrate was removed under reduced pressure to give a light brown solid. Ethyl acetate (5 mL) was added, and the resulted mixture was stirred at 50° C. for 30 min and filtered to give the title compound (0.6 g, purity 95%, yield 25%) as an off-white solid.

¹H NMR (DMSO-d₆, 400 MHz): δ 7.06-7.10 (m, 1H), 7.19 (dd, J=2.4 Hz, 5.6 Hz, 1H), 7.35 (dd, J=2.8 Hz, 12 Hz, 1H), 7.43 (d, J=2.4 Hz, 1H), 7.63 (m, 2H), 8.14 (br, 1H), 8.17 (t, J=8.8 Hz, 1H), 8.53 (d, J=5.6 Hz, 1H), 8.75 (d, J=1.6 Hz, 1H), 8.78 (br, 1H), 9.54 (br, 1H).

MS (ESI, m/z) calcd. for $C_{21}H_{12}D_3ClF_4N_4O_3$: 485, found: 486 [M+H]⁺

Example 6

Preparation of CM4309 based on the intermediate B7 the route using 4-(4-(3-(4-chloro-3-(trifluoromethyl)phenyl)ureido)-3-fluorophenoxy)picolinic acid (the intermediate B7) as the intermediate

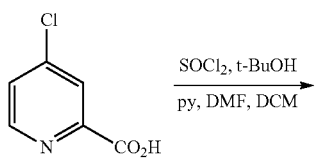

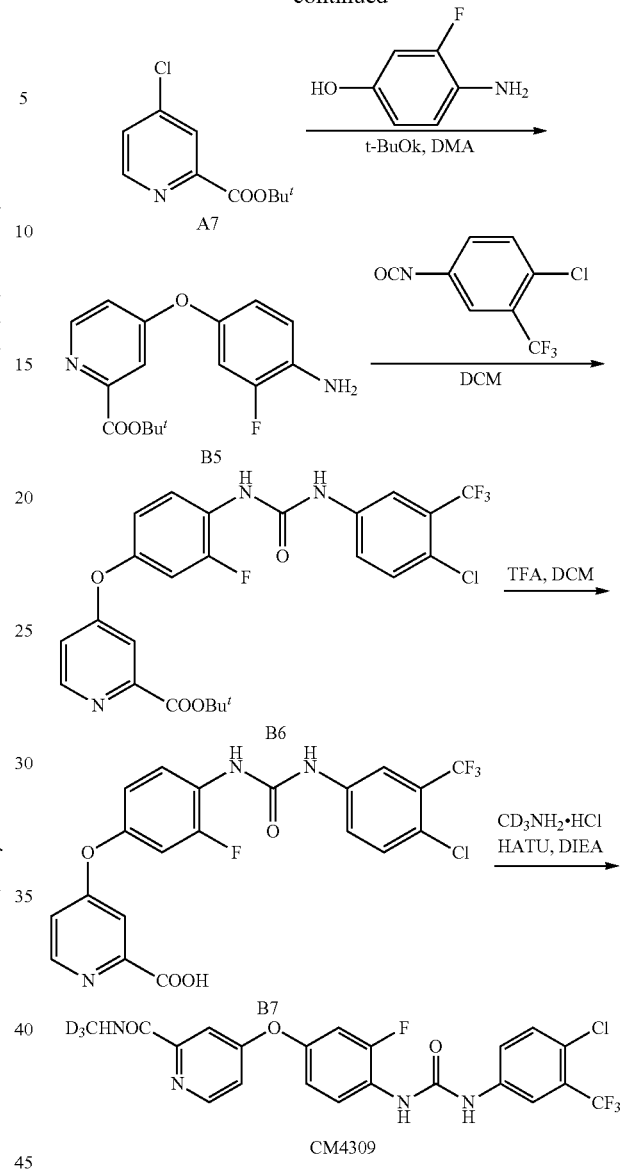

1. Preparation of tert-butyl 4-chloropicolinate 4-chloropicolinic acid (10.5 g, 66.64 mmol) was suspended in thionyl chloride (40 mL). The resulted mixture was heated to 80° C. and refluxed. N,N-dimethyl formamide (0.2 mL) was dropwise added, and the resulted mixture was refluxed for 2 h. Thionyl chloride was removed under reduced pressure to give light yellow acyl chloride. The residue was dissolved in dichloromethane (60 mL). At −40° C., the dichloromethane solution prepared above was added dropwise to a mixed solution of tert-butanol (25 mL), pyridine (20 mL) and dichloromethane (80 mL). The reaction solution was heated to 50° C. and stirred for 16 h. The solvent was removed under reduced pressure, and to the residue was added ethyl acetate (150 mL). The resulted mixture was washed with saturated brine (50 mL×2) and a solution of sodium hydroxide (1 N, 50 mL×2), and then separated. The organic phase was dried over anhydrous sodium sulfate. The solvent in the organic phase was removed under reduced pressure. The residue was dried in vacuum to give the title compound (11.1 g, purity 95%, yield 78%) as a light yellow solid.

¹H NMR (DMSO-d₆, 400 MHz): δ1.56 (s, 9H), 7.80 (dd, J=2.4 Hz, 5.2 Hz, 1H), 8.02 (d, J=2 Hz, 1H), 8.69 (d, J=5.2 Hz, 1H).

MS (ESI, m/z) calcd. for $C_{10}H_{12}ClNO_2$: 213, found: 158 $(M-Bu^t+H)^+$.

2. Preparation of tert-butyl 4-(4-amino-3-fluorophenoxy)picolinate B5

Potassium tert-butoxide (5 g, 23.47 mmol, 1.4 eq) was dissolved in N,N-dimethylacetylamide (DMA, 12 mL). A solution of 3-fluoro-4-aminophenol (4.2 g, 32.86 mmol, 1.4 eq) in DMA (15 mL) was slowly added dropwise at 0° C. After the addition, the mixture was stirred at room temperature for 30 min. The mixture was heated to 100° C. and a solution of tert-butyl 4-chloropicolinate in DMA (18 mL) was slowly added dropwise, and then the mixture was stirred for 1 h. After being cooled to room temperature, ethyl acetate (500 mL) was added, and the resulted mixture was filtered to remove the undissolved material. The filtrate was washed with saturated brine (200 mL×3), dried over anhydrous sodium sulfate. The solvent was removed under reduced pressure to give a brown solid. The crude was purified by column chromatography (petroleum ether: ethyl acetate=3:1) to give the title compound (1.38 g, purity 98%, yield 20%) as a light brown solid.

¹H NMR (CD₃OD, 400 MHz): δ1.61 (s, 9H), 6.78-6.80 (m, 1H), 6.89-6.97 (m, 2H), 7.07 (dd, J=2.4 Hz, 5.6 Hz, 1H), 7.55 (d, J=2.4 Hz, 1H), 8.48 (d, J=5.6 Hz, 1H).

MS (ESI, m/z) calcd. for $C_{16}H_7FN_2O_3$: 304, found: 249 $(M-Bu^t+H)^+$.

3. Preparation of tert-butyl 4-(4-(3-(4-chloro-3-(trifluoromethyl)phenyl)ureido)-3-fluorophenoxy)picolinate B6

At room temperature, 1-chloro-4-isocyanato-2-(trifluoromethyl)benzene (1.06 g, 4.77 mmol, 1.05 eq) was dissolved in dichloromethane (10 mL). A solution of tert-butyl 4-(4-amino-3-fluorophenoxy)picolinate (1.38 g, 4.54 mmol, 1 eq) in dichloromethane (50 mL) was added dropwise slowly. The resulted mixture was stirred at room temperature for 16 h. The solvent was removed under reduced pressure, and the resulted solid was purified by column chromatography (dichloromethane: methanol=30:1) to give the title compound (1.9 g, purity 94%, yield 80%) as a reddish-brown solid.

¹H NMR (DMSO-d₆, 400 MHz): δ1.54 (s, 9H), 7.08 (dd, J=2 Hz, 8.8 Hz, 1H), 7.18 (dd, J=2.8 Hz, 5.6 Hz, 1H), 7.34 (dd, J=2.4 Hz, 3.6 Hz, 1H), 7.46 (d, J=2.4 Hz, 1H), 7.61-7.66 (m, 2H), 8.13-8.19 (m, 2H), 8.58 (d, J=5.6 Hz, 1H), 8.76 (d, J=1.6 Hz, 1H), 9.53 (br, 1H).

MS (ESI, m/z) calcd. for $C_{24}H_{20}ClF_4N_3O_4$: 525, found: 526 $(M+H)^+$.

4. Preparation of 4-(4-(3-(4-chloro-3-(trifluoromethyl)phenyl)ureido)-3-fluorophenoxy)picolinic acid B7

At room temperature, tert-butyl 4-(4-(3-(4-chloro-3-(trifluoromethyl)phenyl)ureido)-3-fluorophenoxy)picolinate (1.8 g, 3.43 mmol) was dissolved in dichloromethane (15 mL). Trifluoroacetic acid (15 mL) and triethyl silane (0.2 mL) was added. The resulted mixture was heated to 50° C. and stirred for 16 h. The solvent was removed under reduced pressure. The residue was partitioned in water (50 mL) and ethyl acetate (50 mL), and separated. The organic phase was removed, and the aqueous layer was filtered. The solid was washed with water (20 mL×2) and dried in vacuum to give the title compound (1.48 g, purity 85%, yield 92%) as a grey solid.

¹H NMR (DMSO-d₆, 400 MHz): δ7.13 (dd, J=1.2 Hz, 9.2 Hz, 1H), 7.38-7.41 (m, 2H), 7.61-7.66 (m, 3H), 8.15 (s, 1H), 8.22 (t, J=8.8 Hz, 1H), 8.67 (d, J=5.6 Hz, 1H), 9.06-9.08 (m, 1H), 10.21-10.28 (m, 1H), 11.96 (br, 1H).

MS (ESI, m/z) calcd. for $C_{20}H_{12}ClF_4N_3O_4$: 469, found: 468 $(M-H)^-$.

5. Preparation of 4-(4-(3-(4-chloro-3-(trifluoromethyl)phenyl]ureido)-3-fluorophenoxy)-N-(methyl-d₃)picolinamide CM4309

Method 1:

At room temperature, 4-(4-(3-(4-chloro-3-(trifluoromethyl)phenyl)ureido)-3-fluorophenoxy)picolinic acid (1.48 g, 3.15 mmol, 1 eq) was dissolved in N,N-dimethylformamide (20 mL). N-(methyl-d₃)amine hydrochloride (0.45 g, 6.29 mmol, 2 eq), 2-(7-aza-1H-benzotriazole-1-yl)-1,1,3,3-tetramethyluronium hexafluoro phosphate (HATU, 2.40 g, 6.29 mmol, 2 eq) and N,N-diisopropylethylamine (DIPEA, 1.20 g, 9.44 mmol, 3 eq) were added. The resulted mixture was stirred at room temperature for 16 h. Water (50 mL) was added dropwise to the above reaction solution. The resulted mixture was stirred for 0.5 h, and filtered to give a light red solid. Ethyl acetate (150 mL) was added, and the resulted mixture was washed with saturated brine (50×3), and separated. The organic phase was dried over anhydrous sodium sulfate and filtered. The solvent in the filtrate was removed under reduced pressure to give CM4309 (1.2 g, purity 97%, yield 79%) as a light red solid.

¹H NMR (DMSO-d₆, 400 MHz): δ 7.06-7.10 (m, 1H), 7.19 (dd, J=2.4 Hz, 5.6 Hz, 1H), 7.35 (dd, J=2.8 Hz, 12 Hz, 1H), 7.43 (d, J=2.4 Hz, 1H), 7.63 (m, 2H), 8.14 (br, 1H), 8.17 (t, J=8.8 Hz, 1H), 8.53 (d, J=5.6 Hz, 1H), 8.75 (d, J=1.6 Hz, 1H), 8.78 (br, 1H), 9.54 (br, 1H).

MS (ESI, m/z) calcd. for $C_{21}H_{12}D_3ClF_4N_4O_3$: 485, found: 486 $[M+H]^+$ Method 2:

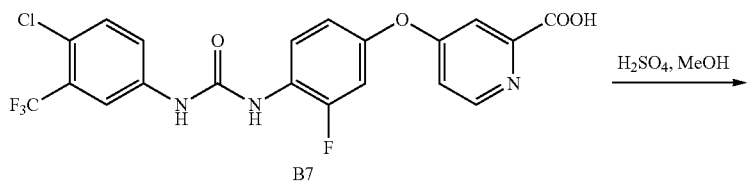

B7

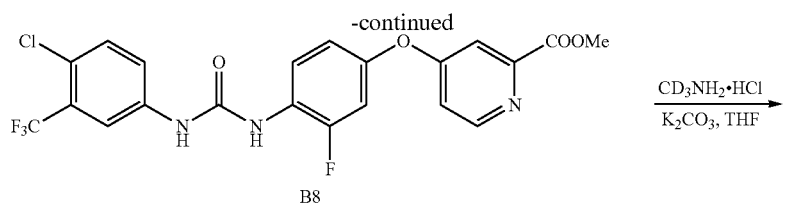

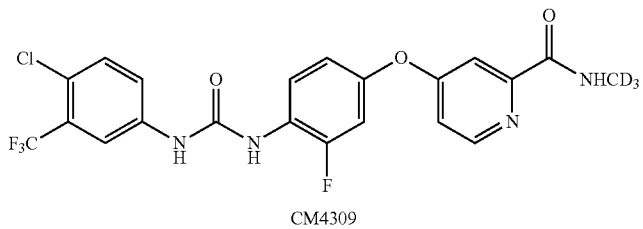

4-(4-(3-(4-chloro-3-(trifluoromethyl)phenyl)ureido)-3-fluorophenoxy)picolinic acid (1 g, 2.13 mmol) was suspended in methanol (20 mL). Concentrated sulfuric acid (5 mL) was added at room temperature. The resulted mixture was refluxed for 3 h. The solvent was removed under reduced pressure, and the residue was purified by column chromatography (dichloromethane: methanol=10:1) to give methyl 4-(4-(3-(4-chloro-3-(trifluoromethyl)phenyl)ureido)-3-fluorophenoxy)picolinate B8 (0.83 g, purity 97%, yield 80%) as a white solid.

MS (ESI, m/z) calcd. for $C_{21}H_{14}ClF_4N_3O_4$: 483, found: 484 $[M+H]^+$

Methyl 4-(4-(3-(4-chloro-3-(trifluoromethyl)phenyl)ureido)-3-fluorophenoxy)picolinate (0.83 g, 1.71 mmol, 1 eq) was placed in a three-necked bottle with tetrahydrofuran (15 mL). N-(methyl-$d_3$)amine hydrochloride (0.24 g, 3.43 mmol, 2 eq) and anhydrous potassium carbonate (0.47 g, 3.43 mmol, 2 eq) were added with agitation. The resulted mixture was stirred at room temperature for 20 h. Water (10 mL) and methyl ten-butyl ether (25 mL) was added, and the resulted mixture was stirred and separated. The aqueous layer was extracted with methyl tert-butyl ether (15 mL). The organic phases were combined, dried over anhydrous sodium sulfate and filtered. The solvent was removed under reduced pressure to give CM4309 (680 mg, purity 95%, yield 82%) as a light red solid.

$^1$H NMR (DMSO-$d_6$, 400 MHz): δ 7.06-7.10 (m, 1H), 7.19 (dd, J=2.4 Hz, 5.6 Hz, 1H), 7.35 (dd, J=2.8 Hz, 12 Hz, 1H), 7.43 (d, J=2.4 Hz, 1H), 7.63 (m, 2H), 8.14 (br, 1H), 8.17 (t, J=8.8 Hz, 1H), 8.53 (d, J=5.6 Hz, 1H), 8.75 (d, J=1.6 Hz, 1H), 8.78 (br, 1H), 9.54 (br, 1H).

MS (ESI, m/z) calcd. for $C_{21}H_{12}D_3ClF_4N_4O_3$: 485, found: 486 $[M+H]^+$

Example 7

Preparation of the Oxide of CM4309 (Compound BO)

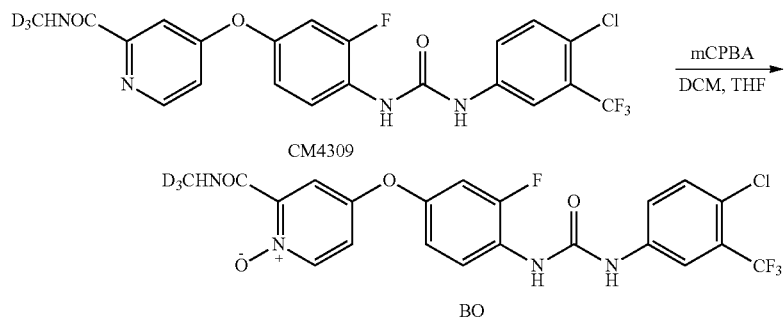

At room temperature, 4-(4-(3-(4-chloro-3-(trifluoromethyl)phenyl]ureido)-3-fluorophenoxy)-N-(methyl-$d_3$) picolinamide (0.5 g, 1.03 mmol, 1 eq) was dissolved in dichloromethane (10 mL) and tetrahydrofuran (10 mL), m-chloroperbenzoic acid (0.54 g, 3.09 mmol, 3 eq) was added. The resulted mixture was heated to 50° C. and stirred for 20 h. The solvent was removed under reduced pressure followed by addition of ethyl acetate (50 mL). The resulted mixture was washed with dilute sodium hydroxide (1 N, 20 mL×2) and saturated brine (20 mL×2) and separated. The organic phase was dried over anhydrous sodium sulfate and filtered. The solvent was removed under reduced pressure, and the residue was purified by column chromatography (ethyl acetate) to give the title compound (0.23 g, purity 95%, yield 45%) as a white solid.

$^1$H NMR (DMSO-$d_6$, 400 MHz): δ 7.10 (dd, J=1.2 Hz, 8.8 Hz, 1H), 7.32-7.38 (m, 2H), 7.61-7.63 (m, 2H), 7.89-7.91 (m, 1H), 8.13-8.17 (m, 2H), 8.42 (d, J=6.8 Hz, 1H), 8.76 (d, J=1.6 Hz, 1H), 9.53 (br, 1H), 11.35 (br, 1H).

MS (ESI, m/z) calcd. for $C_{21}H_{12}D_3ClF_4N_4O_4$: 501, found: 502 $[M+H]^+$.

Example 8

Preparation of the Salt of CM4309

1. Preparation of CM4309 Hydrochloride (4309.HCl)

4-(4-(3-(4-chloro-3-(trifluoromethyl)phenyl]ureido)-3-fluorophenoxy)-N-(methyl-$d_3$)picolinamide (2.5 g, 5.16 mmol, 1 eq) was suspended in ethanol (50 mL), and the mixture was heated and refluxed till it was clear. The mixture was filtered to remove the undissolved material when the mixture was still hot, and then the filtrate was heated to reflux. Concentrated hydrochloride (37%, 6.39 mmol, 0.6 mL, 1.24 eq) was added. The clear solution was kept for about 0.5 min, cooled to room temperature freely after the oil bath was turned off, stirred for 1 h, and filtered to obtain the undissolved substance, dried in vacuum at 50° C. for 20 h to give the title compound (2.56 g, yield 95%) as a light grey solid.

$^1$H NMR (DMSO-d$_6$, 400 MHz): δ7.08-7.10 (m, 1H), 7.24 (dd, J=3.2 Hz, 5.6 Hz, 1H), 7.36 (dd, J=2.8 Hz, 11.6 Hz, 1H), 7.52 (d, J=2.4 Hz, 1H), 7.64 (s, 2H), 8.14 (s, 1H), 8.18 (t, J=9.2 Hz, 1H), 8.56 (d, J=5.6 Hz, 1H), 8.89 (br, 1H), 8.97 (br, 1H), 10.05 (br, 1H), 10.23 (br, 1H).

Melting point: 240° C.-241.5° C.

Elementary analysis: calcd.: C, 48.29%; H, 3.67%; N, 10.73%. found: C, 48.33%; H, 3.20%; N, 10.93%.

2. Preparation of CM4309 Methanesulfonic Acid Ethanol Complex (1:1:1) (4309.MeSO$_3$H.CH$_3$CH$_2$OH)

4-(4-(3-(4-chloro-3-(trifluoromethyl)phenyl]ureido)-3-fluorophenoxy)-N-(methyl-d$_3$)picolinamide (2.1 g, 4.33 mmol, 1 eq) was suspended in ethanol (50 mL), and the resulted mixture was refluxed till it was clear. The mixture was filtered to remove the undissolved substance when the mixture was still hot, and then the filtrate was heated to reflux. Methanesulfonic acid (85%, 8.66 mmol, 0.6 mL, 2 eq) was added. The clear solution was kept for about 0.5 min, cooled to room temperature freely after the oil bath was turned off, stirred for 1 h, and filtered to obtain the undissolved substance, dried in vacuum at 50° C. for 20 h to give the title compound (2.25 g, yield 89%) as a light red solid.

$^1$H NMR (DMSO-d$_6$, 400 MHz): δ1.05 (t, J=6.8 Hz, 3H), 2.48 (s, 3H), 3.44 (q, J=6.8 Hz, 2H), 7.11 (dd, J=1.2 Hz, 8.4 Hz, 1H), 7.31 (dd, J=2.8 Hz, 6 Hz, 1H), 7.38 (dd, J=2.4 Hz, 11.6 Hz, 1H), 7.61-7.65 (m, 3H), 8.14-8.19 (m, 2H), 8.60 (d, J=6 Hz, 1H), 8.90 (t, J=1.2 Hz, 1H), 8.99 (br, 1H), 9.39 (br, 1H), 9.66 (br, 1H).

Melting point: 157.5° C.-158.1° C.

3. Preparation of P-Toluenesulfonate of CM4309 (4309.TsOH)

4-(4-(3-(4-chloro-3-(trifluoromethyl)phenyl]ureido)-3-fluorophenoxy)-N-(methyl-d$_3$)picolinamide (2.16 g, 4.33 mmol, 1 eq) was suspended in ethanol (50 mL), and the mixture was refluxed till the solution was clear. The mixture was filtered when it was still hot to remove the undissolved substance. The filtrate was refluxed till it was clear, and then methanesulfonic acid (70%, 8.66 mmol, 1 mL, 2 eq) was quickly added in one time. The clear solution was kept for about 0.5 min and cooled to room temperature freely after the oil bath was turned off. The mixture was stirred for 1 h and filtered to obtain the undissolved substrate which was dried in vacuum at 50° C. for 20 h to give a white crystal (2.36 g, yield 83%).

$^1$H NMR (DMSO-d$_6$, 400 MHz): δ2.30 (s, 3H), 7.09-7.14 (m, 3H), 7.24 (dd, J=2.4 Hz, 5.2 Hz, 1H), 7.37 (dd, J=2.4 Hz, 11.6 Hz, 1H), 7.48-7.50 (m, 3H), 7.61-7.66 (m, 2H), 8.15-8.19 (m, 2H), 8.56 (d, J=5.6 Hz, 1H), 8.79 (br, 1H), 8.85 (br, 1H), 9.56 (br, 1H), 10.38 (br, 1H).

Melting point: 240.7° C.-241° C.

Example 9

The Activity for Inhibiting c-Kit, PDGFR-β Protein Tyrosine Kinase at the Molecular Level 1. Method:

The activity of diphenylurea compounds for inhibiting c-Kit, PDGFR-β protein tyrosine kinases on molecular level was tested by Enzyme-Linked Immunosorbent Assay (ELISA).

Compounds to be tested: CM4306, CM4308 (4-(4-(3-(4-chloro-3-(trifluoromethyl)phenyl]ureido)-3-fluorophenoxy)-N-methyl-picolinamide) and CM4309.

Main Reagents:

Reacting substrate Poly(Glu,Tyr)$_{4:1}$ was bought from Sigma; Monoclonal antibody against tyrosine phosphate PY99 was bought from Santa Cruz; Horseradish peroxidase labeled sheep-against-rat IgG was bought from Calbiochem; ATP, DTT, OPD were bought from Amresco; microplates were bought from Corning; Su11248 was bought from Merk.

The Testing Method:

See Roskoski, R., Jr. Sunitinib: a VEGF and PDGF receptor protein kinase and angiogenesis inhibitor. Biochem Biophys Res Commun, 356: 323-328, 2007. The details comprise:

Kinase reaction substrate Poly(Glu,Tyr)$_{4:1}$ was diluted to 20 μg/ml by potassium-free PBS, and the microplates were coated. Diphenylurea samples to be tested were added in the wells of the coated microplates (the samples to be tested were made from the stock solution of $10^{-2}$ M in DMSO, and diluted to the desired concentration with reaction buffer before use. The resulted solution was added into the wells to get the final concentration of $10^{-5}$ mol/L in 100 μL reaction system). At the same time, the positive control compound Su11248 was added to the positive control wells.

ATP solution diluted with reaction buffer (the final concentration of ATP is 5 μM) and tyrosine kinase for testing diluted with reaction buffer were added in turn. The total volume of reaction system was 100 μL. At the same time, the negative control wells and the control wells without enzyme were set up.

The reaction system was placed in a wet box and shaked for 1 h at 37° C. by shaking shielding from light. After the reaction was completed, plates were washed three times with T-PBS. Antibody PY99 was added (100 μL/well), and plates were shaked for 30 min at 37° C. After the reaction was completed, the plates were washed with three times T-PBS. Horseradish peroxidase labeled sheep-against-rat IgG was added (100 μL/well), and the plates were shaked for 30 min at 37° C. After the reaction was completed, the plates were washed with T-PBS for three times. OPD developing liquid was added (100 μL/well), and reacted for 1-10 min at room temperature shielding from light. 50 μL of 2 M H$_2$SO$_4$ was added to quench the reaction. A$_{492}$ value was determined using wavelength-adjustable microplates reader VERSAmax.

The inhibition ratio of samples can be calculated by the following formula:

$$\text{inhibition ratio } \% = \left(1 - \frac{OD \text{ value of compound} - OD \text{ value of control without enzyme}}{OD \text{ value of negative control} - OD \text{ value of control without enzyme}}\right) \times 100\%$$

2. Results

| Compound No. | % Inhibition ratio for inhibiting tyrosine kinase at 10 μM | | results |
|---|---|---|---|
| | c-Kit mean value | PDGFR-β mean value | |
| CM4306 | 80.6 | 85.8 | effective |
| CM4308 | 84.0 | 87.1 | effective |
| CM4309 | 85.2 | 88.2 | effective |
| Su11248 (positive drug) | 90.2 | 93.9 | effective |

The above results are the mean values for experiments in duplicate.

3. The Evaluation Standard and the Results

The compound has inhibition efficacy if the inhibition rate of the tested compound at the experimental concentration $10^{-5}$ mol/L was greater than 50%. The compound has no inhibition efficacy if the inhibition rate was less than 50%, provided that the inhibitory activity of the positive control compound meets the reference range.

The results showed that the inhibition ratio of CM4306, CM4308, CM4309 against protein tyrosine kinase c-Kit, PDGFR-β were more than 50%. Therefore, they had significantly inhibitory activity against c-Kit, PDGFR-β tyrosine kinase at the molecular level.

Example 10

The Pharmacokinetic Evaluation of CM4306, CM308 and CM4309 in Rats 3 male SD rats, weighing about 220 g, fasted overnight, were given 4 mg/kg (calculated as free base) of CM4306, CM4308 or CM4309 (the mixed solution of CM4306, CM4308 and CM4309 in PEG400) by intragastric-administration. Blood samples were collected at 0.25, 0.5, 1.0, 2.0, 3.0, 5.0, 7.0, 9.0, 24, 36, 48 and 72 h after the administration. The concentrations of CM4306, CM4308 and CM4309 in plasma were measured by LC/MS/MS.

The Pharmacokinetic Parameters in Rats after Intragastric-Administration of 4 mg/kg CM4306, CM4308 and CM4309

| compound | rat No. | Tmax h | Cmax ng/mL | AUC (0-t) Ng·h/mL | AUC (0-∞) ng·h/mL | MRT (0-∞) h | $T_{1/2}$ h |
|---|---|---|---|---|---|---|---|
| CM4306 | 7 | 8.0 | 642 | 23431 | 24613 | 28.2 | 14.8 |
| | 8 | 2.0 | 1568 | 40239 | 41544 | 23.2 | 12.8 |
| | 9 | 8.0 | 651 | 24571 | 25008 | 23.9 | 10.0 |
| | mean value | 6.0 | 954 | 29414 | 30388 | 25.1 | 12.5 |
| | SD | 3.5 | 532 | 9392 | 9663 | 2.7 | 2.4 |
| CM4308 | 7 | 6.0 | 279 | 9327 | 9541 | 24.1 | 11.7 |
| | 8 | 1.0 | 817 | 18558 | 18973 | 21.7 | 11.4 |
| | 9 | 8.0 | 378 | 11473 | 11605 | 21.0 | 10.1 |
| | mean value | 5.0 | 491 | 13119 | 13373 | 22.2 | 11.1 |
| | SD | 3.6 | 286 | 4831 | 4958 | 1.6 | 0.9 |
| CM4309 | 7 | 24.0 | 470 | 22220 | 27384 | 45.9 | 26.7 |
| | 8 | 1.0 | 933 | 35592 | 41702 | 39.1 | 23.4 |
| | 9 | 8.0 | 530 | 25601 | 28899 | 36.7 | 20.9 |
| | mean value | 11.0 | 644 | 27804 | 32661 | 40.6 | 23.7 |
| | SD | 11.8 | 252 | 6953 | 7866 | 4.8 | 2.9 |

The result showed that, $T_{1/2}$ of CM4309 (23.7 h±2.9 h) was significantly higher than that of CM4306 (12.5 h±2.4 h) and CM4308 (11.1 h±0.9 h).

AUC(0-∞) of CM4309 (32611 ng·h/mL±7866 ng·h/mL) was significantly higher than that of CM4308 (13371 ng·h/mL±4958 ng·h/mL).

Example 11

The In Vivo Pharmacodynamic Evaluation of CM4306, CM4308 and CM4309

The establishment of tumor-bearing nude mice xenograft model: SMMC-7721 cells in logarithmic growth period were cultured. After cell number was counted, the cells were suspended in 1×PBS, and the concentration of the cell suspension was adjusted to $1.5 \times 10^7$/ml. The tumor cells were inoculated (s.c.) $3 \times 10^6$/0.2 ml/mice under the right armpit of nude mice. 45 nude mice were inoculated in total. When the tumor size reached 30-130 mm³, 34 mice were randomly divided into different groups. The difference of the mean value of tumor volume in each group was less than 10%. Administration of testing drugs was started. There were 8 nude mice in each treating group which were given by intragastric-administration at a single dose of 30 mg/kg of CM4306, CM4308 and CM4309 every day for 2 weeks, and 10 nude mice in the control group. Observation continued upon the withdraw till the tumor volume was larger than 2000 mm³. The weight of animals and tumor size were tested twice a week during the experiment. Compounds were dissolved in Cremophor EL/ethanol/water (12.5:12.5:75).

The formula for calculating the tumor volume (TV) is: TV=a×b²/2, wherein a and b independently and respectively represent the length and the breadth of the tumor. The formula for calculating the relative tumor volume (RTV) is: RTV=Vt/$V_0$, wherein $V_0$ is the tumor volume at the beginning of the administration, and Vt is the tumor weight when measured. The index for evaluating the antitumor activity is relative tumor increment rate T/C (%), and the calculation formula is: T/C (%)=($T_{RTV}$/$C_{RTV}$)×100%, wherein, $T_{RTV}$ is the RTV for the treatment group, and $C_{RTV}$ is the RTV for the negative control group.

Evaluation standard for efficacy: it is effective if the relative tumor increment rate T/C (%) is ≤40% and p<0.05 by statistics analysis.

After the administration at 30 mg/kg, T/C % of CM4306 was 64.1%, T/C % of CM4308 was 51.6%, T/C % of CM4309 is 27.0%. Wherein the inhibiting rate of CM4309 at 30 mg/kg was <40%, and tumor volume was significantly different (p<0.01) from the control group, indicating the significant effect in inhibiting tumor growth. At the same dosage, there was no significant difference in tumor volume between CM4306 and CM4308 (p>0.05), but there was significant difference in tumor volume between CM4309 and CM4306 (p<0.05), as well as between CM4309 and CM4308 (p<0.01) (see FIG. 1).

Examples 12-14

Pharmaceutical Compositions

| An active compound | 20 g |
| --- | --- |
| Starch | 140 g |
| Microcrystalline cellulose | 60 g |

Wherein, the active compound independently was CM4309, CM4309 oxide or CM4309 methanesulfonic acid ethanol solvate prepared in Examples 6-8. By routine methods, these substances were blended evenly, and loaded into ordinary gelatin capsules to afford 1000 capsules.

All literatures mentioned in the present application are incorporated by reference herein, as though individually incorporated by reference. Additionally, it should be understood that after reading the above teaching, many variations and modifications may be made by the skilled in the art, and these equivalents also fall within the scope as defined by the appended claims.

What is claimed is:

1. A method for preparing the compound of the following formula,

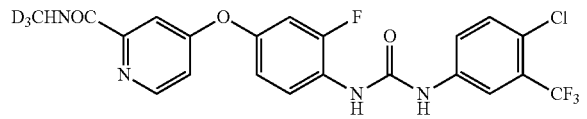

wherein, the method includes:

(a) in an inert solvent and in the presence a base, reacting compound B2 with compound V to form said compound;

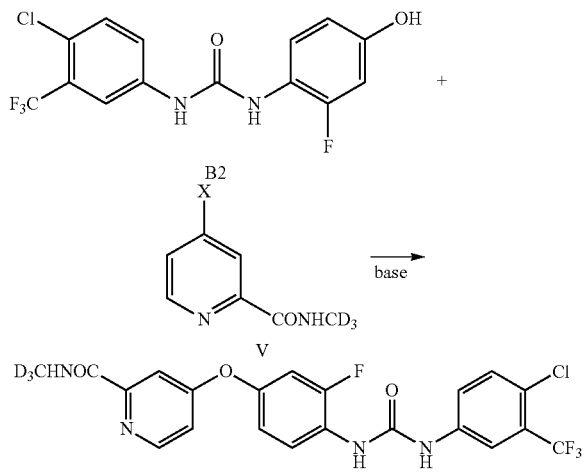

wherein, X is Cl, Br, I, or OSO$_2$CF$_3$;

or, the method includes:

(b) in an inert solvent, reacting compound B' with CD$_3$NH$_2$ or CD$_3$NH$_2$.HCl to form said compound;

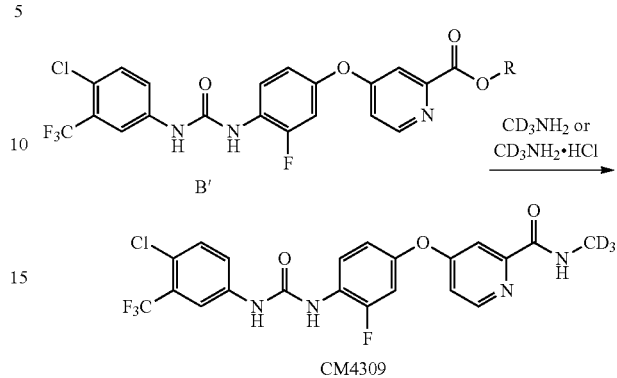

wherein, R is H, straight-chain or branched chain C1-C8 alkyl, or aryl;

or, the method includes:

(c) in an inert solvent, reacting 3-fluoro-4-aminophenol with compound V to form compound B1; in an inert solvent, reacting compound B1 with compound W to form compound M; and in an inert solvent, reacting compound M with 4-chloro-3-trifluoromethylaniline to form said compound;

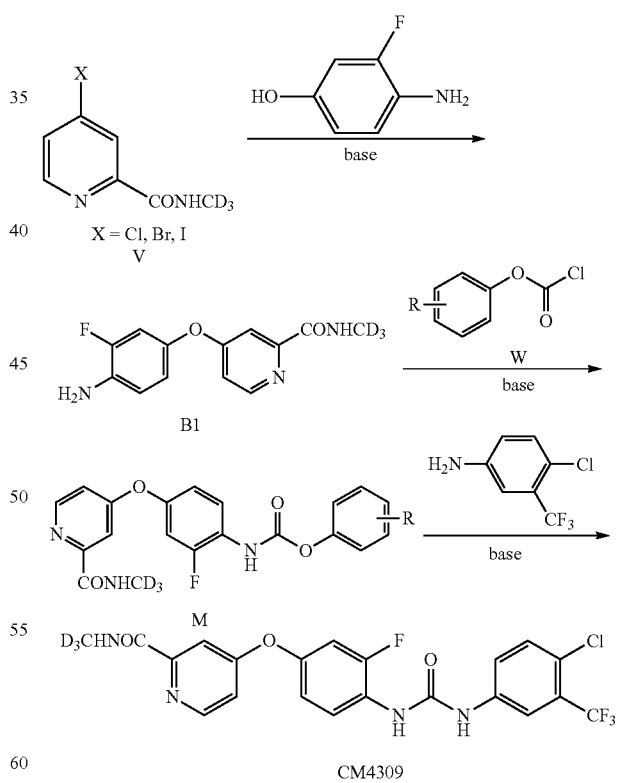

wherein, R is hydrogen, methyl, nitro and chlorine; said inert solvent is selected from chloroform, dichloromethane, tetrahydrofuran, 1,4-dioxane, toluene, pyridine, DMF, DMSO, or the mixed solvent thereof; said base is selected from pyridine, potassium carbonate, sodium carbonate, sodium bicarbonate, potassium bicarbonate, triethylamine, N,N-diethyl isopropyl amine, N,N-dimethylamine pyridine, N-methylmorphine, or the combination thereof;

or, the method includes:

(d) in an inert solvent, reacting 4-chloro-3-trifluoromethylaniline with compound W to form compound B; and in an inert solvent, reacting compound B1 with compound B to form said compound;

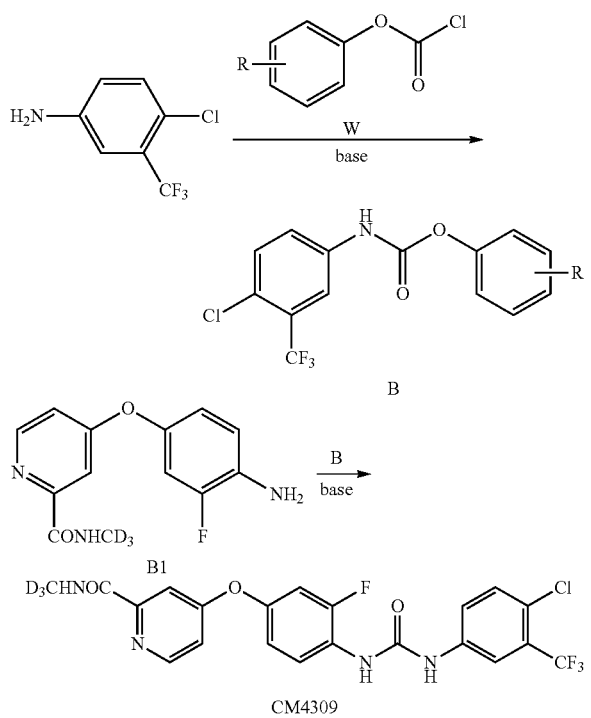

wherein, R is hydrogen, methyl, nitro and chlorine; said inert solvent is selected from chloroform, dichloromethane, tetrahydrofuran, 1,4-dioxane, toluene, pyridine, DMF, DMSO, or the mixed solvent thereof; said base is selected from pyridine, potassium carbonate, sodium carbonate, sodium bicarbonate, potassium bicarbonate, triethylamine, N,N-diethyl isopropyl amine, N,N-dimethylamine pyridine, N-methylmorphine, or the combination thereof.

2. The method according to claim 1, wherein, said compound B2 is prepared through the following method:

in an inert solvent, reacting 3-fluoro-4-aminophenol with 1-chloro-4-isocyanato-2-(trifluoromethyl)benzene to form compound B2;

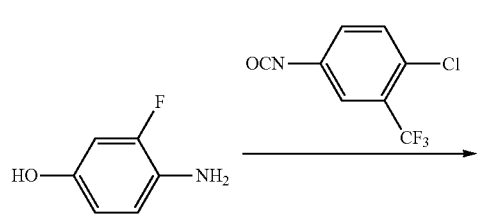

-continued

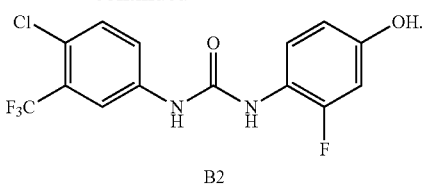

3. The method according to claim 1, wherein, said inert solvent includes: dichloromethane, dichloroethane, acetonitrile, n-hexane, toluene, tetrahydrofuran, N,N-dimethylformamide, N,N-dimethylacetamide, N-methylpyrrolidone, dimethylsulfoxide, or the combination thereof.

4. A method for preparing 4-chloro-N-(methyl-d$_3$)picolinamide, wherein, the method comprises the following step:

under a basic condition and in an inert solvent, reacting methyl 4-chloropicolinate with (methyl-d$_3$)amine or salts thereof to form 4-chloro-N-(methyl-d$_3$)picolinamide

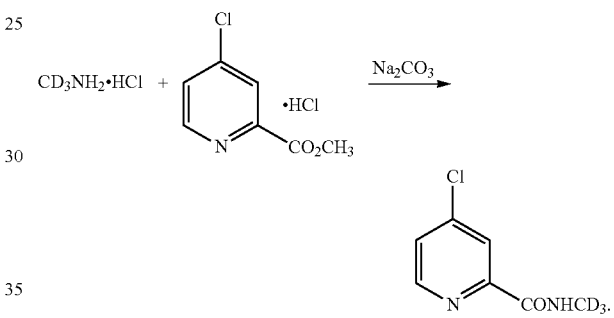

5. A method for preparing compound B2, wherein, the method comprises the step: in an inert solvent, condensing 3-fluoro-4-aminophenol with 1-chloro-4-isocyanato-2-(trifluoromethyl)benzene to form compound B2:

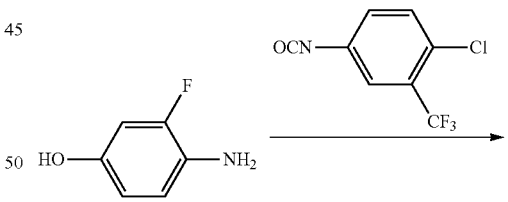

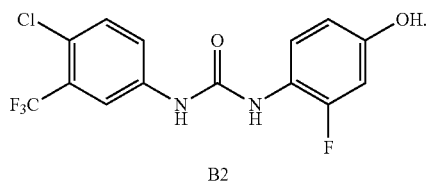

* * * * *